(12) United States Patent
Sugie et al.

(10) Patent No.: US 10,849,712 B2
(45) Date of Patent: Dec. 1, 2020

(54) IMAGE PROCESSING DEVICE, IMAGE PROCESSING METHOD, SURGERY SYSTEM, AND SURGICAL THREAD

(71) Applicant: SONY CORPORATION, Tokyo (JP)

(72) Inventors: Yuki Sugie, Kanagawa (JP); Yasuaki Takahashi, Kanagawa (JP); Yukihiro Nakamura, Kanagawa (JP); Tomoyuki Hirayama, Kanagawa (JP); Kenta Yamaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 392 days.

(21) Appl. No.: 15/759,993

(22) PCT Filed: Sep. 16, 2016

(86) PCT No.: PCT/JP2016/077395
§ 371 (c)(1),
(2) Date: Mar. 14, 2018

(87) PCT Pub. No.: WO2017/057039
PCT Pub. Date: Apr. 6, 2017

(65) Prior Publication Data
US 2018/0250094 A1    Sep. 6, 2018

(30) Foreign Application Priority Data
Sep. 30, 2015 (JP) .................. 2015-194133

(51) Int. Cl.
*A61B 90/00* (2016.01)
*A61B 1/04* (2006.01)
(Continued)

(52) U.S. Cl.
CPC .......... *A61B 90/39* (2016.02); *A61B 1/0005* (2013.01); *A61B 1/00009* (2013.01); *A61B 1/04* (2013.01);
(Continued)

(58) Field of Classification Search
CPC .......... A61B 17/06166; A61B 1/00009; A61B 1/0005; A61B 1/04; A61B 1/043;
(Continued)

(56) References Cited

U.S. PATENT DOCUMENTS 6,293,911 B1    9/2001    Imaizumi et al.
2004/0186351 A1*    9/2004    Imaizumi ............. A61B 5/0071
600/160

(Continued)

FOREIGN PATENT DOCUMENTS

| | | |
|---|---|---|
| JP | 10-201707 A | 8/1998 |
| JP | 2010-95833 A | 4/2010 |
| JP | 2012-85916 A | 5/2012 |
| WO | WO 2013/180127 A1 | 12/2013 |

OTHER PUBLICATIONS

International Search Report dated Nov. 15, 2016 in PCT/JP2016/077395.

*Primary Examiner* — Amelie R Davis
(74) *Attorney, Agent, or Firm* — Xsensus LLP

(57) ABSTRACT

The present technology relates to an image processing device, an image processing method, a surgery system, and a surgical thread capable of further improving visibility of the thread. The image processing device is provided with an image obtaining unit which obtains a first image imaged under an illumination condition in which the surgical thread fluoresces and a second image imaged under an illumination condition including at least visible light as images of an operative site using the surgical thread which fluoresces, and a synthesis unit which generates a synthetic image obtained by synthesizing an area of the surgical thread of the first image and the second image. The present technology is applicable to, for example, a surgery system and the like.

7 Claims, 21 Drawing Sheets

(51) Int. Cl.
  *A61B 34/20*   (2016.01)
  *A61B 1/00*    (2006.01)
  *A61B 1/06*    (2006.01)
  *A61B 1/313*   (2006.01)
  *A61B 17/06*   (2006.01)

(52) U.S. Cl.
  CPC ............ *A61B 1/043* (2013.01); *A61B 1/0653* (2013.01); *A61B 1/3132* (2013.01); *A61B 17/06166* (2013.01); *A61B 34/20* (2016.02); *A61B 2034/2057* (2016.02); *A61B 2034/2065* (2016.02); *A61B 2090/364* (2016.02); *A61B 2090/3941* (2016.02)

(58) Field of Classification Search
  CPC ................ A61B 1/0653; A61B 1/3132; A61B 2034/2057; A61B 2034/2065; A61B 2090/364; A61B 2090/3941; A61B 34/20; A61B 90/39
  See application file for complete search history.

(56) References Cited

U.S. PATENT DOCUMENTS

2011/0319932 A1* 12/2011 Avelar ............. A61B 17/06166
                                                606/228
2015/0148665 A1   5/2015 Sato
2015/0173753 A1*  6/2015 Spivey ..................... D04C 3/40
                                                606/228
2015/0257628 A1*  9/2015 Morita ................... G01B 11/14
                                                382/128

* cited by examiner

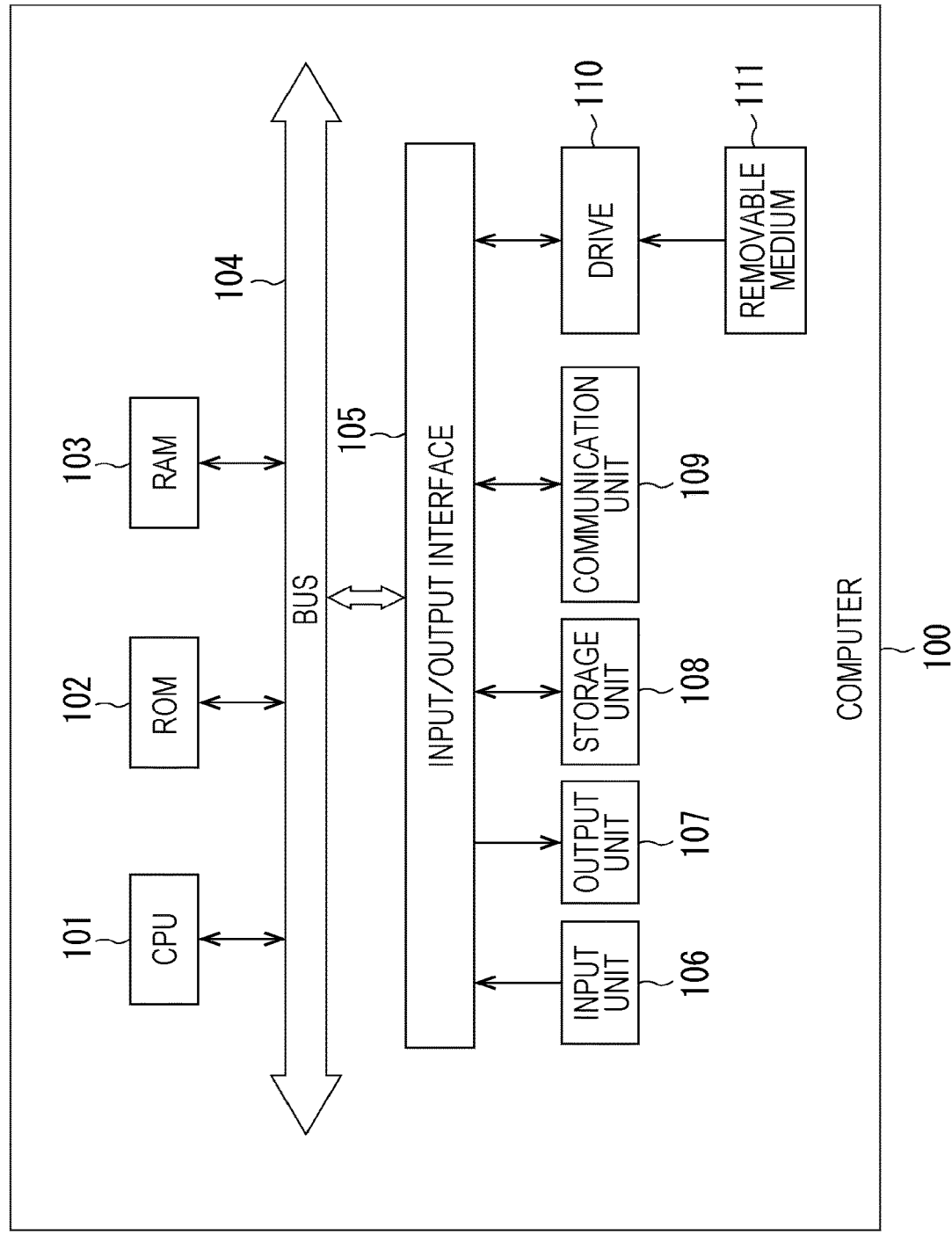

IMAGE PROCESSING DEVICE, IMAGE PROCESSING METHOD, SURGERY SYSTEM, AND SURGICAL THREAD

TECHNICAL FIELD

The present technology relates to an image processing device, an image processing method, a surgery system, and a surgical thread, and especially relates to the image processing device, the image processing method, the surgery system, and the surgical thread capable of further improving visibility of the thread.

BACKGROUND ART

For example, in a surgical operation and the like, the visibility of a suture thread is improved by making a color of the suture thread a color different from that in a living body (for example, black or purple). However, there is a limit in improving the visibility by merely imparting the color due to an effect of a small diameter of the suture thread to be used and the like.

On the other hand, a technology of improving the visibility by allowing the thread itself to shine is also developed (refer to, for example, Patent Document 1).

CITATION LIST

Patent Document

Patent Document 1: Japanese Patent Application Laid-Open No. 2010-95833

SUMMARY OF THE INVENTION

Problems to be Solved by the Invention

However, there also is a limit in improving the visibility by merely allowing the thread itself to fluoresce.

The present technology is achieved in view of such a situation and an object thereof is to further improve the visibility of the thread.

Solutions to Problems

An image processing device according to a first aspect of the present technology is provided with an image obtaining unit which obtains a first image imaged under an illumination condition in which a surgical thread fluoresces and a second image imaged under an illumination condition including at least visible light as images of an operative site using the surgical thread which fluoresces, and a synthesis unit which generates a synthetic image obtained by synthesizing an area of the surgical thread of the first image and the second image.

An image processing method according to the first aspect of the present technology is provided with steps of obtaining a first image imaged under an illumination condition in which a surgical thread fluoresces and a second image imaged under an illumination condition including at least visible light as images of an operative site using the surgical thread which fluoresces, and generating a synthetic image obtained by synthesizing an area of the surgical thread of the first image and the second image.

In the first aspect of the present technology, a first image imaged under an illumination condition in which a surgical thread fluoresces and a second image imaged under an illumination condition including at least visible light are obtained as images of an operative site using the surgical thread which fluoresces, and a synthetic image obtained by synthesizing an area of the surgical thread of the first image and the second image is generated.

A surgery system according to a second aspect of the present technology is provided with an imaging unit which images a first image imaged under an illumination condition in which a surgical thread fluoresces and a second image imaged under an illumination condition including at least visible light as images of an operative site using the surgical thread which fluoresces, and a synthesis unit which generates a synthetic image obtained by synthesizing an area of the surgical thread of the first image and the second image.

In the second aspect of the present technology, a first image imaged under an illumination condition in which a surgical thread fluoresces and a second image imaged under an illumination condition including at least visible light are imaged as images of an operative site using the surgical thread which fluoresces, and a synthetic image obtained by synthesizing an area of the surgical thread of the first image and the second image is generated.

A surgical thread according to a third aspect of the present technology fluoresces in a pattern not present in a living body.

In the third aspect of the present technology, this fluoresces in a pattern not present in a living body.

The image processing device may be an independent device or may be an internal block which forms one device.

Effects of the Invention

According to the first to third aspects of the present technology, it is possible to further improve the visibility of the thread.

Meanwhile, the effects are not necessarily limited to those herein described, and may include any of the effects described in the present disclosure.

BRIEF DESCRIPTION OF DRAWINGS

FIG. 21 is a block diagram illustrating a configuration example of one embodiment of a computer to which the present technology is applied.

MODE FOR CARRYING OUT THE INVENTION

Figure 1:
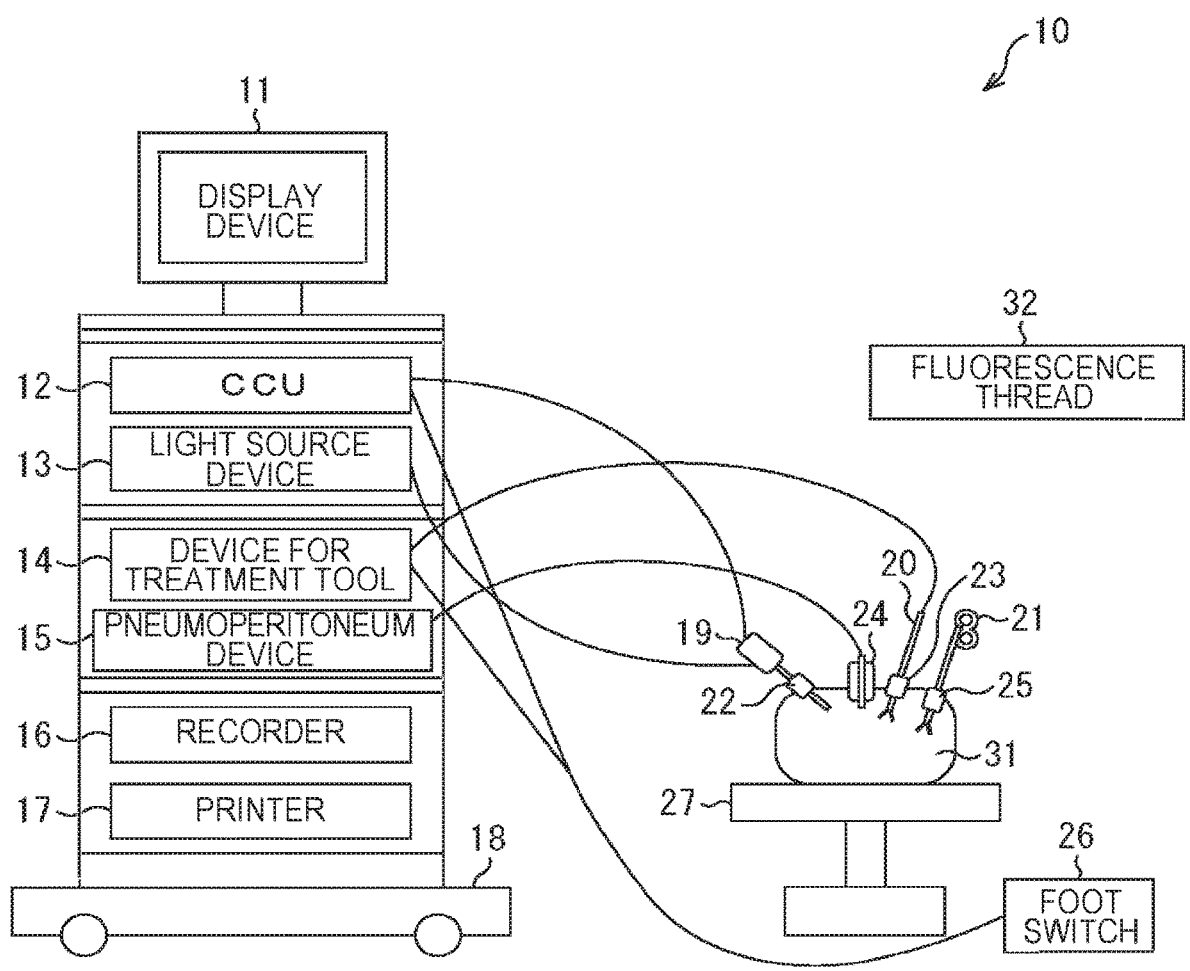
FIG. 1 is a view illustrating a configuration example of an endoscopic surgery system to which the present technology is applied.

Modes for carrying out the present technology (hereinafter, referred to as embodiments) are hereinafter described. Meanwhile, the description is given in the following order.
 1. First Embodiment (Example of Separately Imaging Special Light Image and Normal Light Image)
 2. Second Embodiment (Example of Generating Special Light Image and Normal Light Image from One Image)
  3. Other Configuration Example of Fluorescent Thread
  4. Variation of Synthesis Unit
  5. Other Application Example of Color Conversion Processing
  6. Fluorescent Thread Area Pixel Addition Processing 1. First Embodiment <Configuration Example of Endoscopic Surgery System>
FIG. 1 is a view illustrating a configuration example of an endoscopic surgery system to which the present technology is applied.

An endoscopic surgery system 10 is provided with a cart 18 on which a display device 11, a camera control unit (CCU) 12, a light source device 13, a device for treatment tool 14, a pneumoperitoneum device 15, a recorder 16, and a printer 17 are mounted. The endoscopic surgery system 10 also includes an endoscope (laparoscope) 19, an energy treatment tool 20, forceps 21, trocars 22 to 25, a foot switch 26, and a patient bed 27. The endoscopic surgery system 10 arranged in an operating room, for example, supports an operator who performs laparoscopic surgery on an affected site included in an abdomen 31 of a patient lying on the patient bed 27.

Specifically, the display device 11 of the endoscopic surgery system 10 includes a stationary 2D display, a head-mounted display and the like. The display device 11 displays an image of an operative site and the like supplied from the CCU 12.

The CCU 12 (image processing device) is connected to the endoscope 19 via a camera cable. Meanwhile, the CCU 12 may also be wirelessly connected to the endoscope 19. The CCU 12 receives an image of a site to be operated (hereinafter also referred to as an operative site image) imaged by the endoscope 19 and transmitted via the camera cable, and supplies the same to the display device 11. The CCU 12 supplies the received operative site image to the recorder 16 and the printer 17 as needed.

The light source device 13 is connected to the endoscope 19 via a light guide cable. The light source device 13 switches light of various wavelengths and emits the same to the endoscope 19.

The device for treatment tool 14 being a high-frequency output device is connected to the energy treatment tool 20 and the foot switch 26 via cables. The device for treatment tool 14 outputs high-frequency current to the energy treatment tool 20 in response to an operation signal supplied from the foot switch 26.

The pneumoperitoneum device 15 provided with air supply means and air suction means supplies air in the abdomen 31 through a hole of the trocar 24 being a hole making tool attached to an abdominal wall of the abdomen 31.

The recorder 16 records the operative site image supplied from the CCU 12. The printer 17 prints the operative site image supplied from the CCU.

The endoscope 19 is inserted into the abdomen 31 to be operated through a hole of the trocar 22 attached to the abdominal wall of the abdomen 31. The endoscope 19 irradiates the inside of the abdomen 31 with the light emitted from the light source device 13, and images the inside of the abdomen 31 as the operative site image. The endoscope 19 supplies the operative site image obtained by an imaging unit 41 to the CCU 12 via the camera cable.

The energy treatment tool 20 (treatment device) includes an electric scalpel and the like. The energy treatment tool 20 is inserted into the abdomen 31 through a hole of the trocar 23 attached to the abdominal wall of the abdomen 31. The energy treatment tool 20 denatures or cuts the inside of the abdomen 31 using electric heat.

The forceps 21 are inserted into the abdomen 31 through a hole of the trocar 25 attached to the abdominal wall of the abdomen 31. The forceps 21 grasp the inside of the abdomen 31. The endoscope 19, the energy treatment tool 20, and the forceps 21 are grasped by the operator, an assistant, a scopist, a robot or the like.

The foot switch 26 accepts an operation by a foot of the operator, the assistant and the like. The foot switch 26 supplies the operation signal indicating the accepted operation to the CCU 12 and the device for treatment tool 14.

By using the endoscopic surgery system 10, the operator may excise the affected site in the abdomen 31 without performing abdominal surgery in which the abdominal wall is cut and the abdomen is opened.

While watching a processed image displayed on the display device 11 on the basis of the image imaged by the imaging unit 41 of the endoscope 19, the operator treats the affected site (operative site) in the abdomen 31 to be operated. At that time, a fluorescent thread 32 is used for suturing and knotting the affected site. The fluorescent thread 32 is a thread which fluoresces in a case where a condition of illumination irradiating the affected site is a predetermined condition; for example, a silk thread which shines with green fluorescent protein disclosed in Patent Document 1 described above may be used.

The fluorescent thread 32 has a characteristic of fluorescing so that this is easily visually recognized; in contrast, the illumination condition under which the fluorescent thread 32 fluoresces often is a state in which the operator has difficulty in seeing the affected site, for example, a dark state in which visible light is not used.

Therefore, the CCU 12 of the endoscopic surgery system 10 controls the light source device 13 and the endoscope 19 so as to perform imaging under the illumination condition where the operator may easily visually recognize the fluorescent thread 32 and perform imaging under the illumination condition where the operator may easily visually recognize the affected site. The CCU 12 also performs image synthesis processing of a plurality of operative site images obtained under a plurality of illumination conditions, thereby generating a synthetic image in which the visibility of the fluorescent thread 32 is improved and allows the display device 11 to display the same. The operator may perform an operation while watching the synthetic image displayed on the display device 11, thereby smoothly performing a suturing work and a knotting work.

<Block Diagram Relating to Image Processing>

Figure 2:
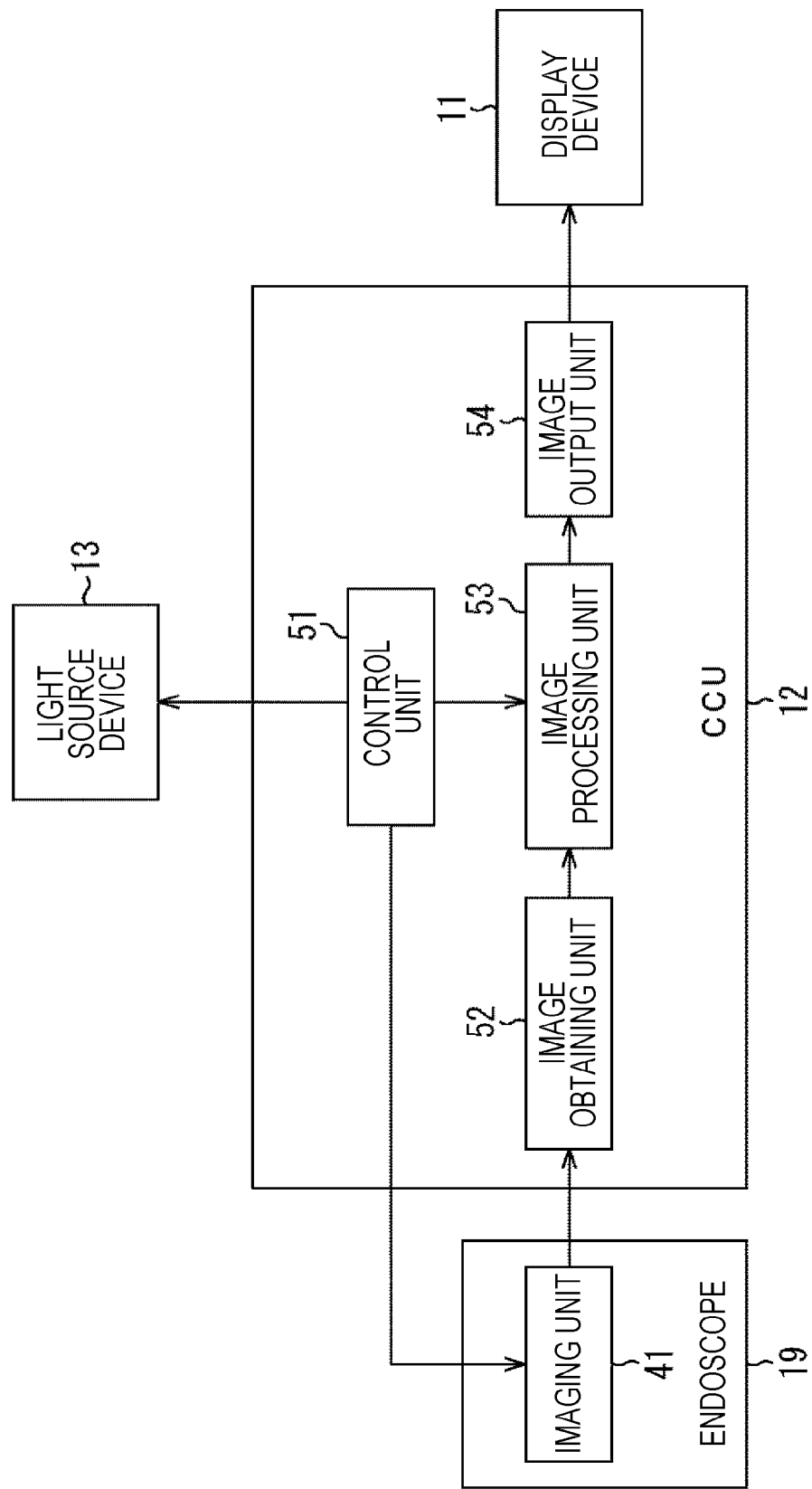
FIG. 2 is a block diagram related to image processing of the endoscopic surgery system.

FIG. 2 is a block diagram focusing on a block relating to imaging under the illumination condition in which the fluorescent thread 32 is easily visually recognized, the imaging under the illumination condition in which the affected site is easily visually recognized, and the image processing of a plurality of operative site images obtained under a plurality of illumination conditions.

The CCU 12 is at least provided with a control unit 51, an image obtaining unit 52, an image processing unit 53, and an image output unit 54.

The control unit 51 performs illumination control to switch between the illumination under the illumination condition in which the fluorescent thread 32 is easily visually recognized and the illumination under the illumination condition in which the affected site is easily visually recognized in accordance with timing of imaging by the imaging unit 41 of the endoscope 19 on the light source device 13.

The control unit 51 also controls imaging timing by the imaging unit 41 of the endoscope 19. The endoscope 19 is provided with an optical system such as an illumination lens and the imaging unit 41. The imaging unit 41 includes a CMOS sensor of Bayer array in which four pixels of R, G, R, and B pixels are repeatedly arranged, for example. The imaging unit 41 images on the basis of the imaging timing controlled by the control unit 51 and outputs the image of the affected site obtained as a result to the image obtaining unit 52.

Meanwhile, hereinafter, the illumination under the illumination condition in which the fluorescent thread 32 is easily visually recognized is referred to as the special light, and the illumination under the illumination condition in which the affected site is easily visually recognized is referred to as the normal light. The special light is, for example, ultraviolet light referred to as so-called black light, infrared light (IR light) and the like. The normal light is, for example, white light (visible light).

Also, an image imaged in a state irradiated with the special light is referred to as a special light image, and an image imaged in a state irradiated with the normal light is referred to as a normal light image.

The control unit 51 controls switching between the special light and the normal light emitted from the light source device 13. Furthermore, the control unit 51 outputs an irradiation identification signal indicating which of the images obtained by irradiation with the normal light and the special light is supplied from the image obtaining unit 52 to the image processing unit 53 to the image processing unit 53.

In addition to the above-described control, the control unit 51 controls an operation of an entire endoscopic surgery system 10, for example, controls the device for treatment tool 14 and the pneumoperitoneum device 15 based on the operation signal supplied from the foot switch 26, and controls the recorder 16 and the printer 17.

The image obtaining unit 52 obtains the normal light image and the special light image supplied from the imaging unit 41 and supplies the same to the image processing unit 53.

The image processing unit 53 performs predetermined image processing on the normal light image and the special light image supplied from the image obtaining unit 52 and supplies the processed image to the image output unit 54.

For example, the image processing unit 53 detects a motion vector using two normal light images at different imaging timings. The image processing unit 53 also performs predetermined filter processing on the special light image, thereby generating an image obtained by extracting a portion of the fluorescent thread 32 in the special light image (hereinafter referred to as a fluorescent thread extracted image). Furthermore, on the basis of the motion vector detected from the normal light image, the image processing unit 53 performs motion correction of the fluorescent thread extracted image, synthesizes the motion-corrected fluorescent thread extracted image and the normal light image, and outputs the synthetic image obtained as a result to the image output unit 54.

The image output unit 54 converts the synthetic image supplied from the image processing unit 53 to a signal of a predetermined format which the display device 11 may accept, and outputs the same to the display device 11. On the basis of the image signal supplied from the image output unit 54, the display device 11 displays the synthetic image generated so that the operator may easily visually recognize the affected site and the fluorescent thread 32.

Figure 3:
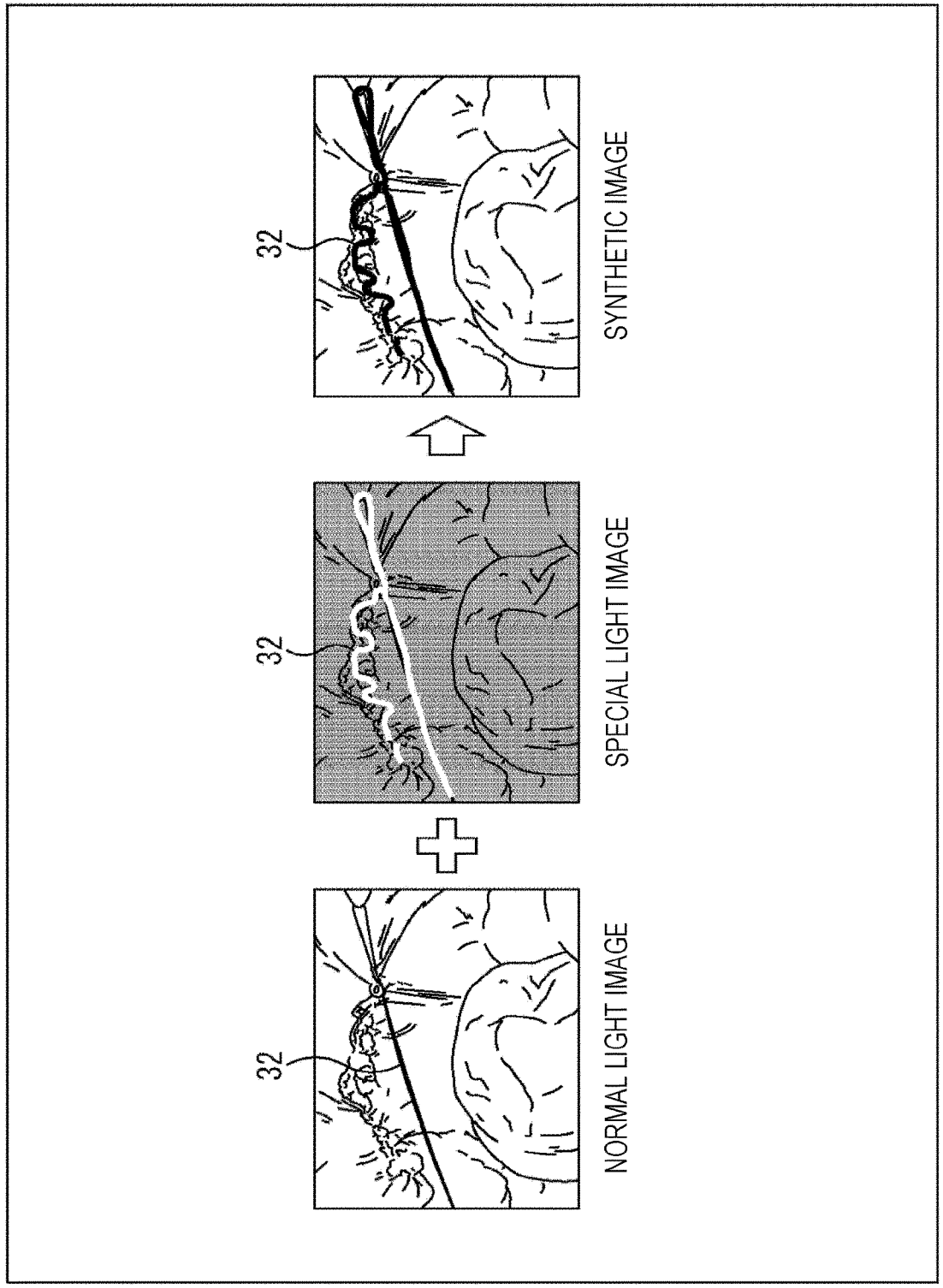
FIG. 3 is a view explaining image synthesis processing.

FIG. 3 is a view conceptually illustrating the image synthesis processing performed by the image processing unit 53.

The normal light image is, for example, the image imaged with irradiation of the white light, the image in which the affected site is easily visually recognized but the fluorescent thread 32 is not easily seen.

On the other hand, the special light image is, for example, the image imaged with irradiation of the IR light, the image in which the fluorescent thread 32 is easily visually recognized but the affected site is not easily seen.

The synthetic image obtained by synthesizing the normal light image and the special light image is the image using the image of the normal light image for the affected site and using the image of the special light image for the fluorescent thread 32. As a result, both the affected site and the fluorescent thread 32 are easy visually recognized in the images.

<Imaging Timing of Normal Light Image and Special Light Image>

Figure 4:
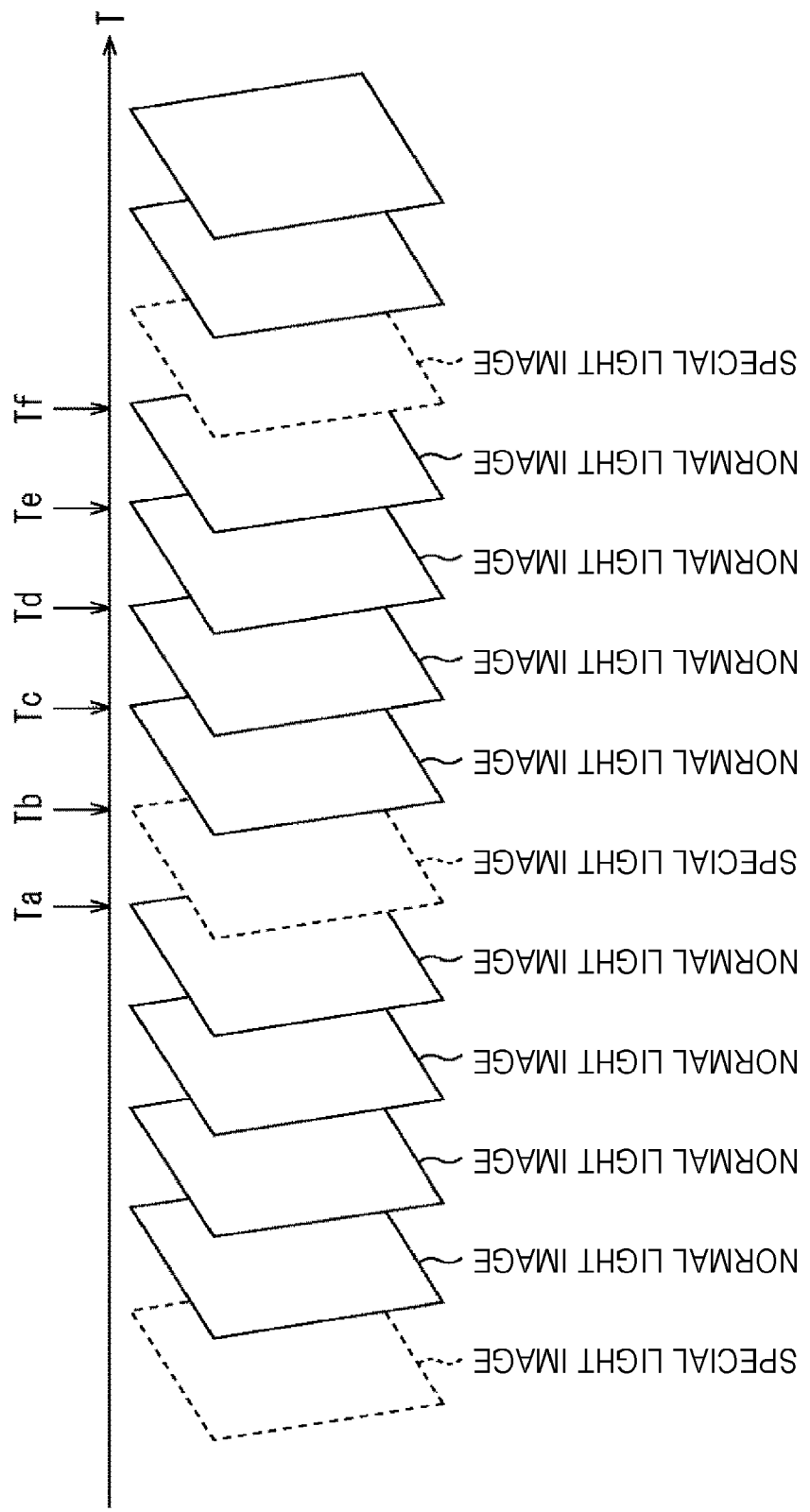
FIG. 4 is a view explaining imaging timings of a normal light image and a special light image.

Next, FIG. 4 illustrates an example of the imaging timings of the normal light image and the special light image.

The control unit 51 controls to continuously image several frames of the normal light images and then image the special light image. A ratio of imaging of the normal light images and the special light images is, for example, 4:1 as illustrated in FIG. 4. However, this ratio is not limited to 4:1 and may be changed.

Time Ta in FIG. 4 indicates the timing at which the normal light image is imaged one frame before the special light image is imaged, and time Tb indicates the timing at which the special light image is imaged. Times Tc, Td, Te, and Tf indicate the timings at which the normal light image is imaged one, two, three, and four frames after the special light image is imaged, respectively.

<Detailed Configuration Example of Image Processing Unit 53>

Figure 5:
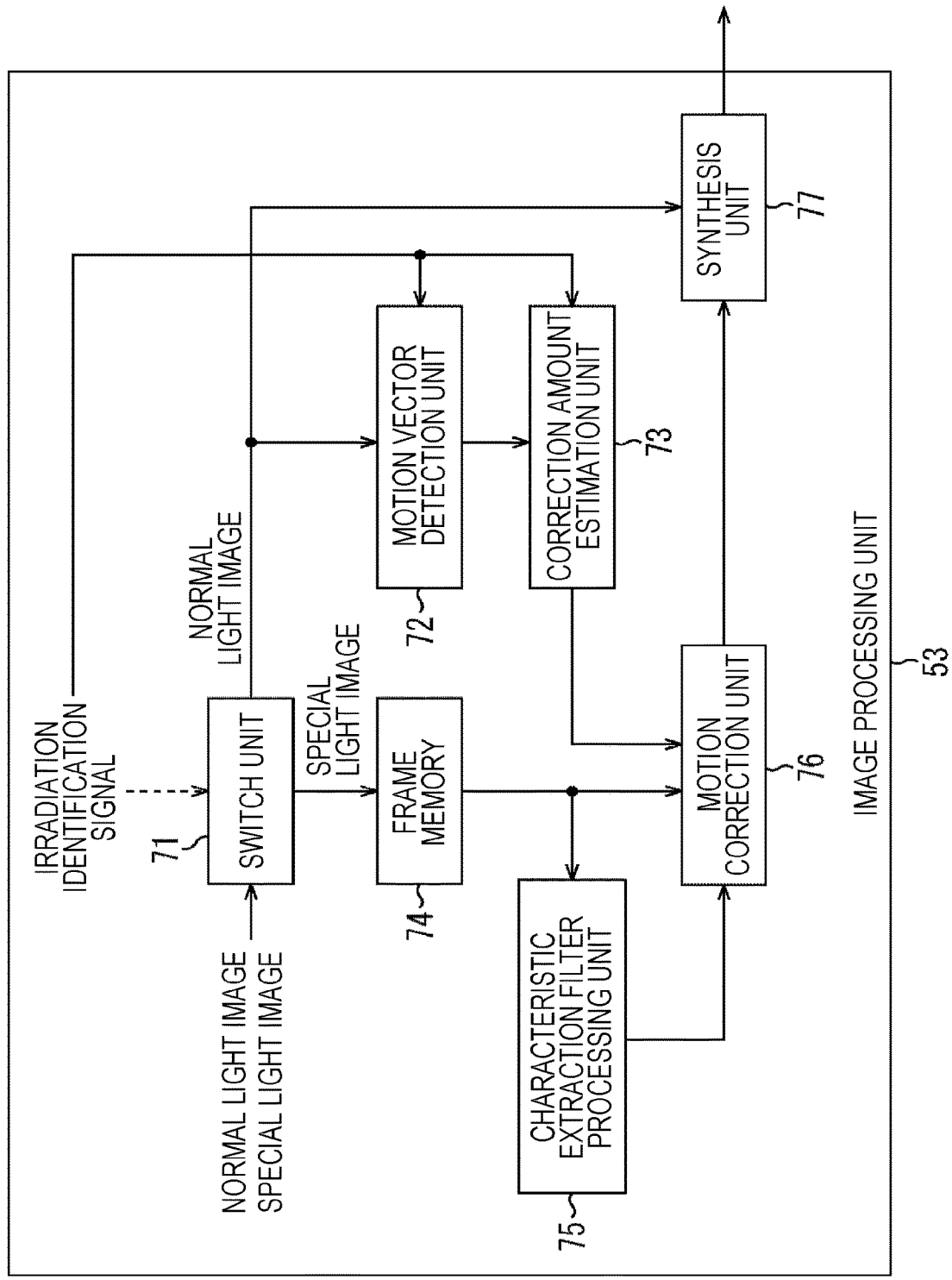
FIG. 5 is a block diagram illustrating a detailed configuration example of an image processing unit.

FIG. 5 is a block diagram illustrating a detailed configuration example of the image processing unit 53.

The image processing unit 53 includes a switch unit 71, a motion vector detection unit 72, a correction amount estimation unit 73, a frame memory 74, a characteristic extraction filter processing unit 75, a motion correction unit 76, and a synthesis unit 77.

In the image processing unit 53, the normal light image and the special light image input from the image obtaining unit 52 are input to the switch unit 71, and the irradiation identification signal from the control unit 51 is input to the switch unit 71, the motion vector detection unit 72, and the correction amount estimation unit 73.

On the basis of the irradiation identification signal, the switch unit 71 determines whether the input from the image obtaining unit 52 is the special light image, and in a case where this is not the special light image (this is the normal light image), outputs the same to the motion vector detection unit 72 and the synthesis unit 77, and in a case of the special light image, outputs the same to the frame memory 74.

The motion vector detection unit 72 detects the motion vector using two normal light images with different imaging timings for each frame period, and outputs the detected motion vector to the correction amount estimation unit 73.

On the basis of the motion vector detected by the motion vector detection unit 72, the correction amount estimation unit 73 estimates the motion correction amount of the special light image and the fluorescent thread extracted image, and outputs the estimated motion correction amount to the motion correction unit 76. Meanwhile, the correction amount estimation unit 73 may correct the motion vector which might be erroneously detected on the basis of the continuously detected motion vectors and estimate the motion correction amount on the basis of the corrected motion vector.

The frame memory 74 holds the special light image input from the switch unit 71 and supplies the held special light image to the characteristic extraction filter processing unit 75 and the motion correction unit 76 every frame period. Also, in a case where the next special light image is input from the switch unit 71, the frame memory 74 updates the held special light image.

The characteristic extraction filter processing unit 75 extracts an area of the fluorescent thread 32 on the basis of the characteristic of the fluorescent thread 32 in the special light image supplied from the frame memory 74 and generates the fluorescent thread extracted image illustrating an extraction result. More specifically, for example, the characteristic extraction filter processing unit 75 extracts an area within a specific range in which a signal level of a pixel corresponds to a fluorescent color, that is, an area having a specific RGB level, and generates the fluorescent thread extracted image illustrating the extracted result.

Meanwhile, the frame memory 74 supplies the held special light image every frame period as described above, so that the same special light image is continuously supplied. In this case, the characteristic extraction filter processing unit 75 may output a result of the previous characteristic extraction filter processing as it is to the motion correction unit 76 while omitting the characteristic extraction filter processing.

As the characteristic extraction filter processing, the characteristic extraction filter processing unit 75 may execute processing other than the processing of extracting the area having the specific RGB level described above, for example, differential filter processing (for example, Sobel filter processing), contour detection processing, processing based on variance, dynamic range and the like in each minute block of (3×3) set in the image. That is, the characteristic extraction filter processing performed by the characteristic extraction filter processing unit 75 is not limited as long as this may extract the area of the fluorescent thread 32.

On the basis of the motion correction amount input from the motion correction amount estimation unit 73, the motion correction unit 76 performs the motion correction of the special light image from the frame memory 74, and performs the motion correction of the fluorescent thread extracted image from the characteristic extraction filter processing unit 75, and outputs the motion-corrected special light image and fluorescent thread extracted image to the synthesis unit 77.

The synthesis unit 77 performs the synthesis processing of synthesizing the normal light image and the motion-corrected fluorescent thread extracted image, thereby generating the synthetic image, and outputs the same to the image output unit 54. For example, the synthesis unit 77 generates the synthetic image in which the image of the normal light image is used for the part of the affected site and the image of the special light image is used for the fluorescent thread 32. Also, for example, the synthesis unit 77 generates the synthetic image by superimposing a portion of the fluorescent thread 32 in the special light image on the normal light image. In this manner, it is possible to generate the synthetic image in which both the affected site and the fluorescent thread 32 may be easily visually recognized as illustrated in FIG. 3.

Meanwhile, in addition to the normal light image and the motion-corrected fluorescent thread extracted image, the motion-corrected special light image is also input to the synthesis unit 77, so that the motion-corrected special light image may also be used in the synthesis processing as needed.

<Detailed Configuration Example of Motion Vector Detection Unit 72>

Figure 6:
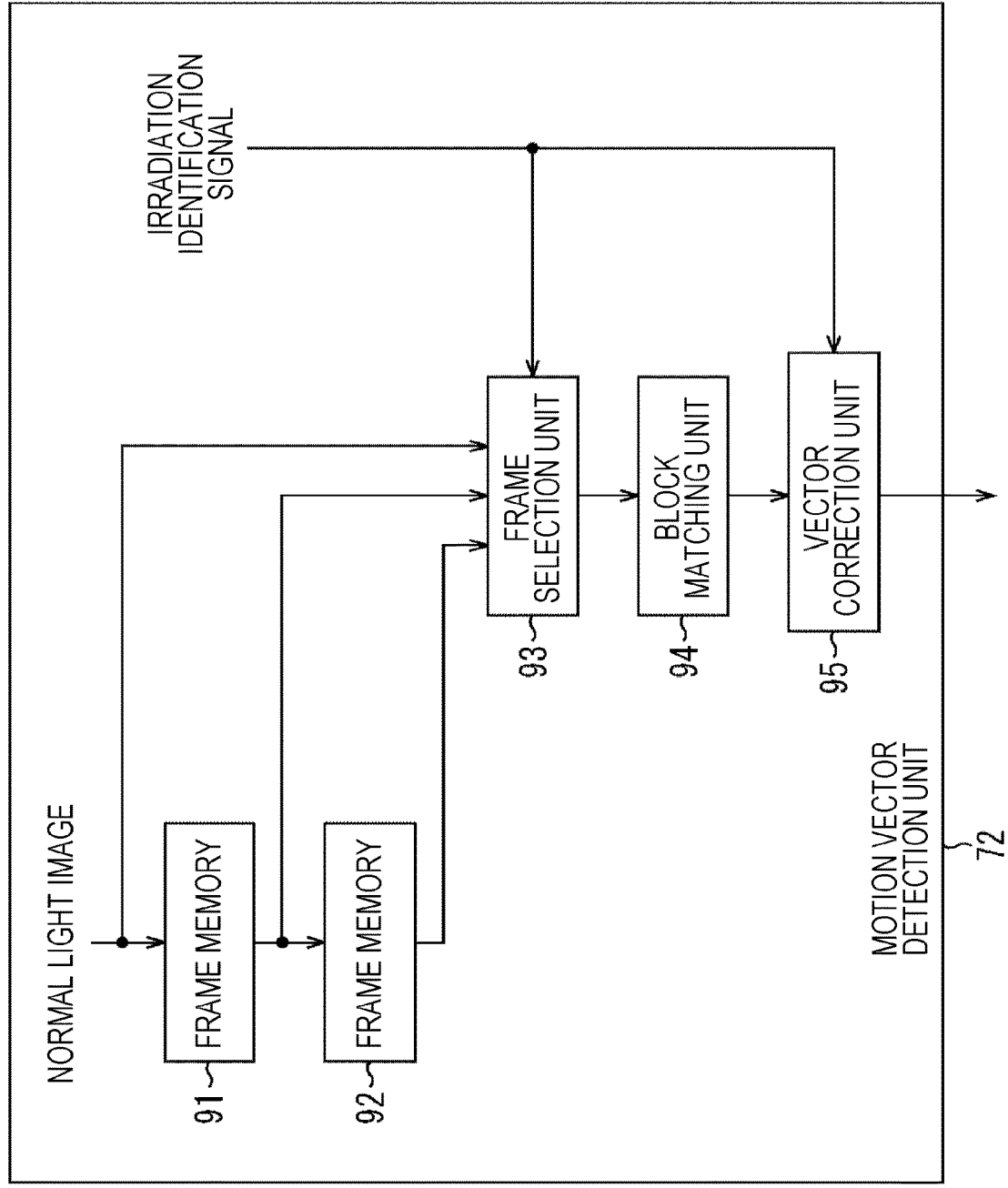
FIG. 6 is a block diagram illustrating a detailed configuration example of a motion vector detection unit.

FIG. 6 is a block diagram illustrating a detailed configuration example of the motion vector detection unit 72.

The motion vector detection unit 72 includes frame memories 91 and 92, a frame selection unit 93, a block matching unit 94, and a vector correction unit 95.

In the motion vector detection unit 72, the normal light image input from the switch unit 71 on a preceding stage is input to the frame memory 91 and the frame selection unit 93.

For each frame period, the frame memory 91 outputs the normal light image held so far to the frame memory 92 and the frame selection unit 93, and updates the held data by the normal light image input from the switch unit 71 on the preceding stage. Similarly, for each frame period, the frame memory 92 outputs the normal light image held so far to the frame selection unit 93 and updates the held data by the normal light image input from the frame memory 91 on the preceding stage.

However, in the frame period, at the timing at which the normal light image is not input to the motion vector detection unit 72, the frame memory 91 outputs the normal light image held so far to a subsequent stage and clears the data held so far.

At a next timing, the frame memory 91 does not output data to the subsequent stage because there is no held data. The frame memory 92 outputs the normal light image held so far to the subsequent stage and clears the data held so far.

Therefore, two or three normal light images of different imaging timings are simultaneously input to the frame selection unit 93.

In a case where the two normal light images are simultaneously input, the frame selection unit 93 outputs the two normal light images to the block matching unit 94. Also, in a case where three normal light images are simultaneously input, the frame selection unit 93 outputs the two normal light images input from the frame memories 91 and 92 to the block matching unit 94. The block matching unit 94 detects the motion vector between the two normal light images by block matching processing.

On the basis of the irradiation identification signal, the vector correction unit 95 determines a relationship between the two normal light images used for the motion vector, corrects the detected motion vector on the basis of the relationship, and outputs the motion vector to the correction amount estimation unit 73.

The correction of the motion vector by the vector correction unit 95 is specifically described.

With reference to the output from the frame memory 91, in a case where reference imaging timing is the time Ta illustrated in FIG. 4, the normal light image one frame before the reference and the reference normal light image are input from the frame memory 92 and the frame memory 91, respectively, to the frame selection unit 93, and the motion vector is detected from the two normal light images. In this case, the vector correction unit 95 does not correct the motion vector.

In a case where the reference imaging timing is the time Tb illustrated in FIG. 4, since the time Tb is the imaging timing of the special light image, the frame memory 91 does not output. Then, the normal light image at the time Ta one frame before the reference and the normal light image at the time Tc one frame after the reference are input from the frame memory 92 and the switch unit 71, respectively, to the frame selection unit 93, and the motion vector is detected from the two normal light images. In this case, since the detected motion vector is that between the normal light images separated by two frames, the vector correction unit 95 multiplies each of vertical and horizontal components of the detected motion vector by ½.

In a case where the reference imaging timing is the time Tc illustrated in FIG. 4, the reference normal light image and the normal light image at the time Td one frame after the reference are input from the frame memory 91 and the switch unit 71, respectively, to the frame selection unit 93 and the motion vector is detected from the two normal light images. In this case, since a direction of the detected motion vector is opposite to that in other cases, the vector correction unit 95 multiplies each of the vertical and horizontal components of the detected motion vector by −1.

In a case where the reference imaging timing is the time Td illustrated in FIG. 4, the normal light image at the time Tc one frame before the reference, the reference normal light image, and the normal light image at the time Te one frame after the reference are input from the frame memory 92, the frame memory 91, and the switch unit 71, respectively, to the frame selection unit 93 and the motion vector is detected from the two normal light images from the frame memories 91 and 92. In this case, the vector correction unit 95 does not correct the motion vector.

In a case where the reference imaging timing is the time Te illustrated in FIG. 4, the normal light image at the time Td one frame before the reference, the reference normal light image, and the normal light image at the time Tf one frame after the reference are input from the frame memory 92, the frame memory 91, and the switch unit 71, respectively, to the frame selection unit 93 and the motion vector is detected from the two normal light images from the frame memories 91 and 92. In this case, the vector correction unit 95 does not correct the motion vector.

The motion vector corrected in the above-described manner is output from the vector correction unit 95 to the correction amount estimation unit 73 on the subsequent stage.

<Flowchart of Image Synthesis Processing>

The image synthesis processing by the image processing unit 53 is next described with reference to a flowchart in FIG. 7. This image synthesis processing is executed every frame period.

At step S1, the switch unit 71 determines whether the input from the image obtaining unit 52 is the special light image or the normal light image on the basis of the irradiation identification signal, and switches an output destination of the input image. That is, in a case where the switch unit 71 determines that the input from the image obtaining unit 52 is the special light image, this outputs the special light image to the frame memory 74. On the other hand, in a case where the switch unit 71 determines that the input from the image obtaining unit 52 is not the special light image (the normal light image), this outputs the normal light image to the motion vector detection unit 72 and the synthesis unit 77.

At step S2, the frame memory 74 supplies the special light image held so far to the characteristic extraction filter processing unit 75 and the motion correction unit 76. Also, in a case where the special light image is input from the switch unit 71, the frame memory 74 updates the held special light image.

At step S3, the characteristic extraction filter processing unit 75 performs predetermined characteristic extraction filter processing on the special light image supplied from the frame memory 74, thereby generating the fluorescent thread extracted image obtained by extracting the area of the fluorescent thread 32 in the image and outputs the same to the motion correction unit 76.

At step S4, the motion vector detection unit 72 detects the motion vector using two normal light images at different imaging timings, and outputs the same to the correction amount estimation unit 73.

At step S5, the correction amount estimation unit 73 determines whether the detected motion vector is equal to or smaller than a predetermined threshold, and in a case where this is equal to or smaller than the predetermined threshold, the procedure shifts to step S6 so as to use the motion vector for the motion correction. On the contrary, in a case where the detected motion vector is larger than the predetermined threshold, the motion vector is not used for the motion correction. In this case, the image synthesis processing corresponding to the imaging timing of this time ends.

At step S6, on the basis of the motion vector detected by the motion vector detection unit 72, the correction amount estimation unit 73 estimates the motion correction amounts of the special light image and the fluorescent thread extracted image, and outputs the estimated motion correction amounts to the motion correction unit 76. Specifically, for example, as represented by following equation (1), the motion correction amounts $H_x$ and $H_y$ are calculated.

[Equation 1]

$$H_x = \sum_{t=1}^{N} V_{x,t}$$

$$H_y = \sum_{t=1}^{N} V_{y,t} \qquad (1)$$

In equation (1), $V_x$ and $V_y$ represent the detected and corrected motion vectors, and N represents the imaging timing t=N of the normal light image in which the motion vector is detected with respect to the imaging timing t=0 of the special light image to be corrected.

Meanwhile, the correction amount estimation unit 73 may also estimate the motion correction amount after correcting variation of the motion vectors on the basis of a series of motion vectors as described below as another method of estimating the motion correction amount.

Figure 8:
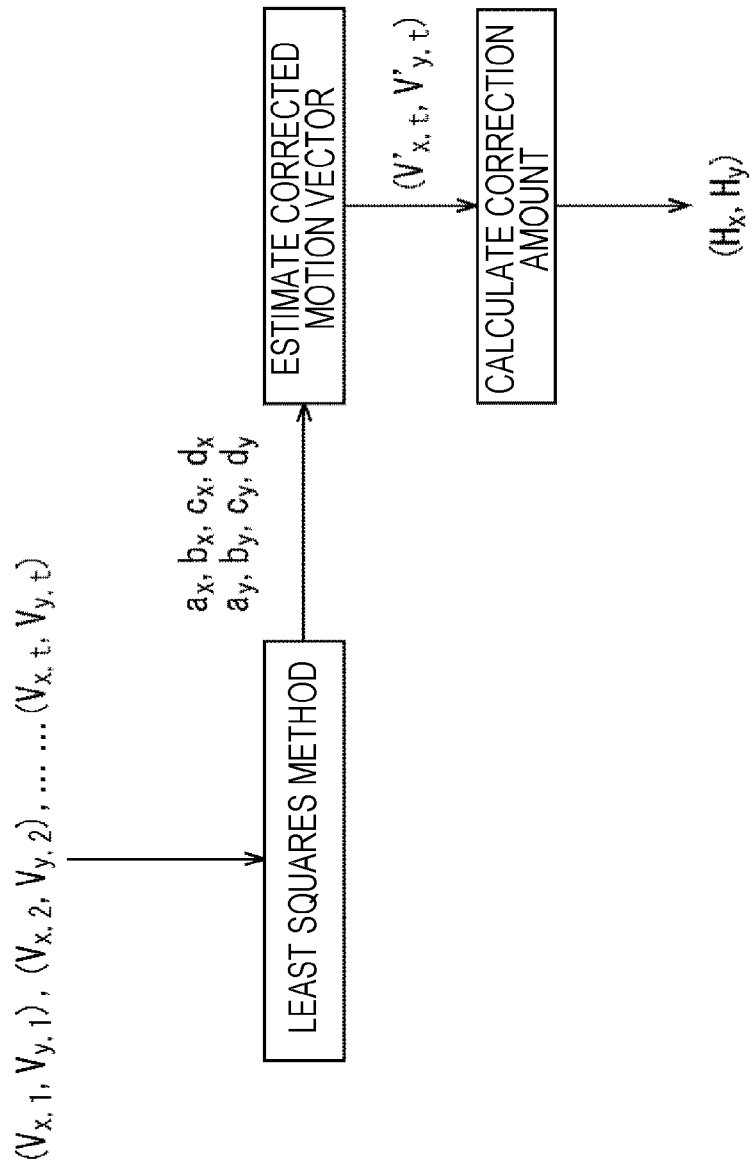
FIG. 8 is a view explaining a flow of processing of estimating a motion correction amount.
Figure 9:
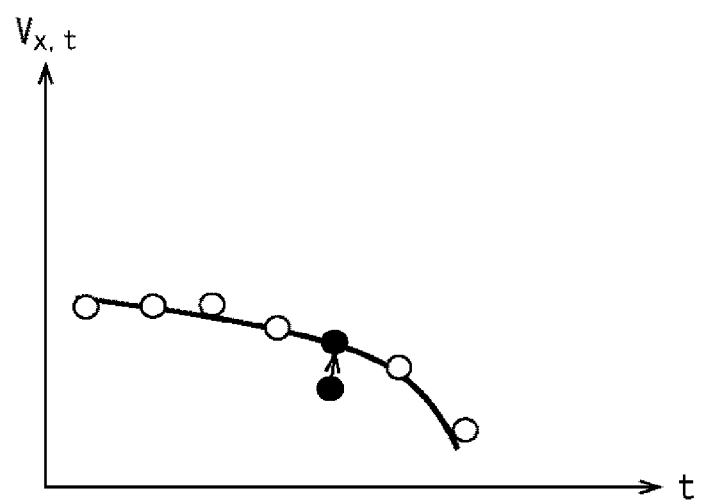
FIG. 9 is a view illustrating an image of correcting variation of motion vectors.

FIG. 8 illustrates a flow of processing of estimating the motion correction amount after correcting the variation of the motion vectors on the basis of a series of motion vectors. FIG. 9 illustrates an image of correcting the variation in motion vectors on the basis of a series of motion vectors.

Specifically, the correction amount estimation unit 73 estimates the motion vector $(V'_{x,t}, V'_{y,t})$ for the imaging timing t as represented by following equation (2).

[Equation 2]

$$V'_{x,t} = a_x t^3 + b_x t^2 + c_x t + d_x$$

$$V'_{y,t} = a_y t^3 + b_y t^2 + c_y t + d_y \qquad (2)$$

Then, the correction amount estimation unit 73 substitutes the motion vector of equation (1) with the estimated motion vector $(V'_{x,t}, V'_{y,t})$ and calculates the motion correction amounts $H_x$ and $H_y$ by following equation (3)

[Equation 3]

$$H_x = \sum_{t=1}^{N} V'_{x,t}$$

$$H_y = \sum_{t=1}^{N} V'_{y,t} \qquad (3)$$

Meanwhile, coefficients $(a_x, b_x, c_x, d_x)$ and $(a_y, b_y, c_y, d_y)$ in equation (2) may be calculated by the least squares method by using the detected motion vectors $(V_{x,1}, V_{y,1}), \ldots,$ and $(V_{x,t}, V_{y,t})$ After the motion correction amount is estimated as described above, the procedure shifts to step S7.

At step S7, on the basis of the motion correction amount input from the motion correction amount estimation unit 73, the motion correction unit 76 performs the motion correction of the special light image from the frame memory 74, performs the motion correction of the fluorescent thread extracted image from the characteristic extraction filter processing unit 75, and outputs the motion-corrected special light image and fluorescent thread extracted image to the synthesis unit 77. In the normal light image, the special light image, and the fluorescent thread extracted image input to the synthesis unit 77, objects in respective images are accurately aligned.

At step S8, the synthesis unit 77 performs the synthesis processing of the normal light image and the motion-corrected fluorescent thread extracted image, and outputs the synthetic image obtained as a result to the image output unit 54. For example, briefly, the synthesis unit 77 extracts pixels having luminance or chrominance equal to or larger than a predetermined threshold in the fluorescent thread extracted image as the area of the fluorescent thread 32. Then, the synthesis unit 77 generates the synthetic image in which the pixel value of the fluorescent thread extracted image is adopted for the extracted area of the fluorescent thread 32 and the pixel value of the normal light image is adopted for the other area and make the same the synthetic image.

In addition, the synthesis unit 77 may also perform the following synthesis processing, for example.

[Equation 4]

$$O_R(x,y) = C_0 \times N_R(x,y) + C_1 \times \text{Feature}_R(x,y) \times I_R(x,y)$$

$$O_G(x,y) = C_0 \times N_G(x,y) + C_1 \times \text{Feature}_G(x,y) \times I_G(x,y)$$

$$O_B(x,y) = C_0 \times N_B(x,y) + C_1 \times \text{Feature}_B(x,y) \times I_B(x,y) \qquad (4)$$

In equation (4), O(x,y) represents the pixel value of the synthetic image, N(x,y) represents the pixel value of the normal light image, Feature(x,y) represents the pixel value of the motion-corrected fluorescent thread extracted image, and I(x,y) represents the pixel value of the motion-corrected special light image. $C_0$ and $C_1$ are coefficients for controlling a degree of superimposition, and may be arbitrarily set by the user. In the synthesis processing of equation (4), a result of multiplication of the motion-corrected fluorescent thread extracted image and special light image is added to the normal light image.

The synthesis unit 77 may also perform the following synthesis processing, for example.

[Equation 5]

$$\begin{pmatrix} O_R(x,y) \\ O_G(x,y) \\ O_B(x,y) \end{pmatrix} =$$

$$\begin{pmatrix} C_{1R} \times \text{Feature}_R(x,y) & C_{1G} \times \text{Feature}_G(x,y) & C_{1B} \times \text{Feature}_B(x,y) \\ C_{2R} \times \text{Feature}_R(x,y) & C_{2G} \times \text{Feature}_G(x,y) & C_{1B} \times \text{Feature}_B(x,y) \\ C_{3R} \times \text{Feature}_R(x,y) & C_{3G} \times \text{Feature}_G(x,y) & C_{1B} \times \text{Feature}_B(x,y) \end{pmatrix} \begin{pmatrix} N_R(x,y) \\ N_G(x,y) \\ N_B(x,y) \end{pmatrix} \qquad (5)$$

In equation (5), O(x,y) represents the pixel value of the synthetic image, N(x,y) represents the pixel value of the normal light image, Feature(x,y) represents the pixel value of the motion-corrected fluorescent thread extracted image, and C represents a color conversion coefficient. In the synthesis processing of equation (5), pseudo color conversion is performed on the normal light image by color matrix processing using the color conversion coefficients C multiplied by the pixel values of the fluorescent thread extracted image.

According to the image synthesis processing described above, since the motion vector is detected by using only the normal light image and the motion correction amount is estimated after correcting the detected motion vector, the motion correction of the special light image and the fluorescent thread extracted image may be executed accurately. As a result, it is possible to precisely align the area of the fluorescent thread 32 in the special light image with respect to the normal light image and to generate the synthetic image with improved visibility. Since the generated synthetic image is displayed on the display device 11, it is possible to present to the operator the image in which both the affected site and the fluorescent thread 32 may be easily visually recognized.

Figure 10:
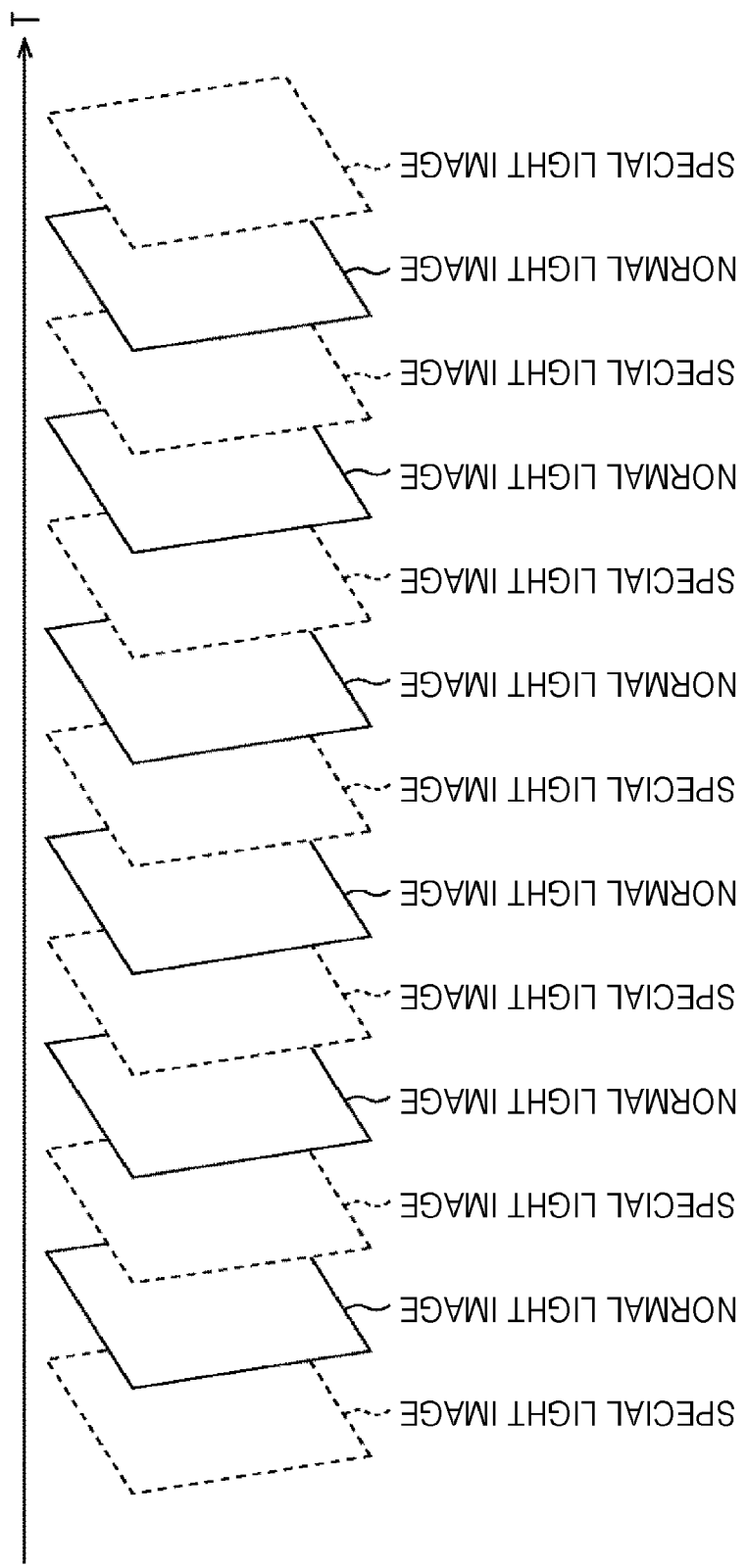
FIG. 10 is a view explaining another example of the imaging timings of the normal light image and the special light image.

Meanwhile, although the example in which the light source device 13 is controlled so that one special light image is obtained for four normal light images is described as illustrated in FIG. 4 in the example described above, the ratio of imaging of the normal light images and the special light images is not limited thereto. For example, as illustrated in FIG. 10, the control unit 51 may control so that the normal light image and the special light image are alternately obtained.

2. Second Embodiment

Next, a second embodiment is described. Meanwhile, in the following description, descriptions of the same part as that described so far are omitted, and only different parts will be described.

In the first embodiment described above, the imaging unit 41 includes the CMOS sensor having the general Bayer array and the like, the special light image by the special light and the normal light image by the normal light are generated by changing the illumination condition of the light source device 13, and the synthetic image is generated by using the special light image and the normal light image.

Figure 11:
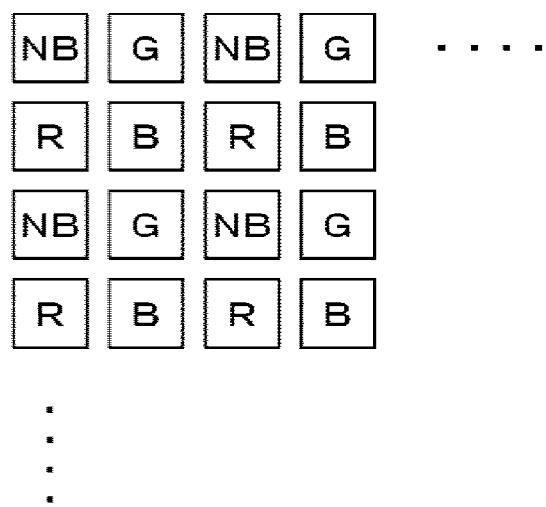
FIG. 11 is a view explaining an image sensor of an imaging unit according to a second embodiment.

In the second embodiment, as an image sensor of an imaging unit 41, a sensor provided with a pixel sensitive to light of a narrow band wavelength as illustrated in FIG. 11 is adopted.

The image sensor illustrated in FIG. 11 is a sensor having a pixel array in which four pixels of NB, G, R, and B are repeatedly arranged. In the second embodiment, a fluorescent thread 32 is a thread which emits light of a specific narrow band wavelength under white light. The NB pixel is the pixel sensitive to the light of the narrow band wavelength emitted by the fluorescent thread 32.

Figure 12:
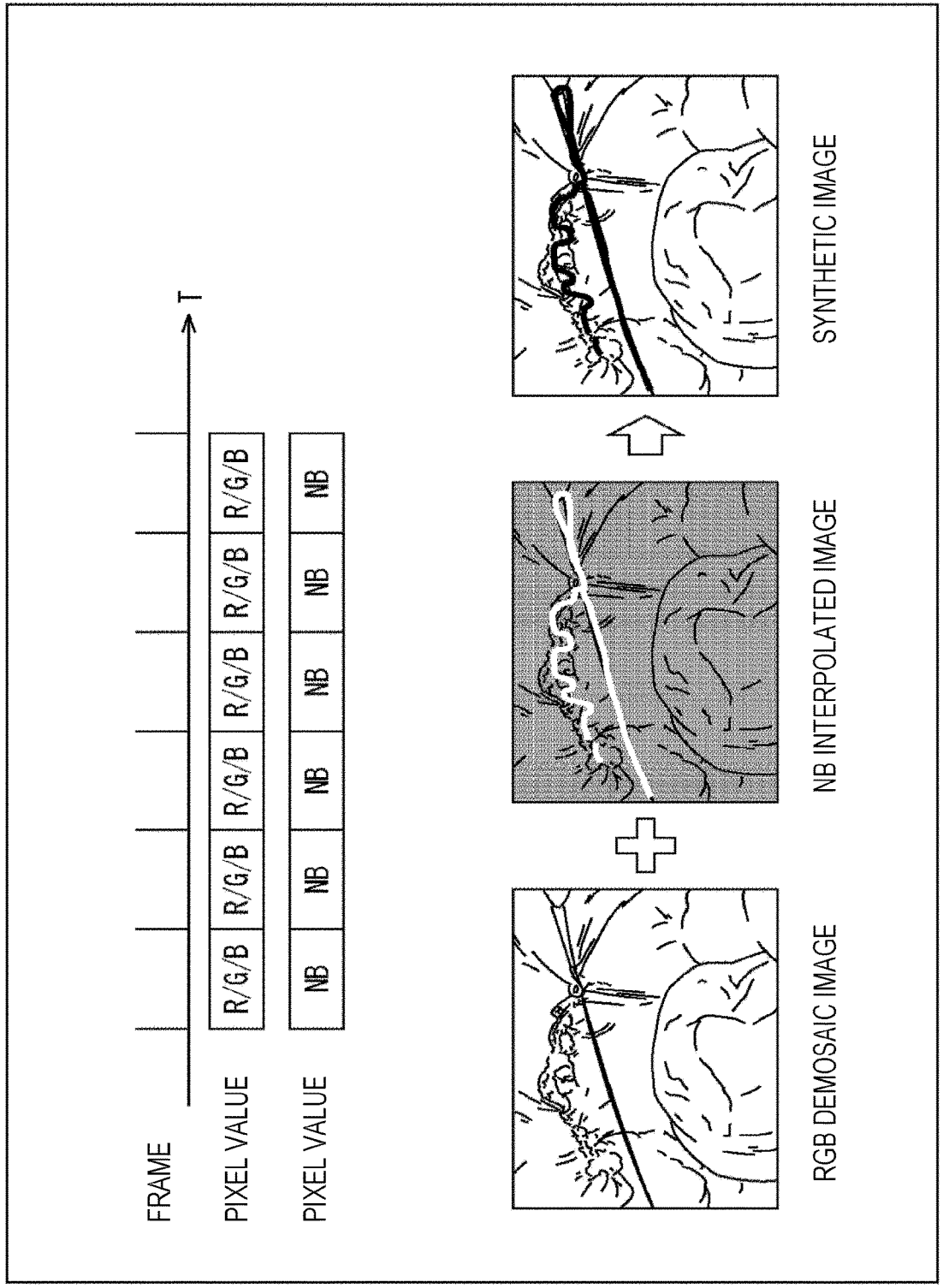
FIG. 12 is a view explaining an image synthesis processing according to the second embodiment.

In a case where the imaging unit 41 is provided with such image sensor, as illustrated in FIG. 12, both a pixel value for forming an image in which an operator may easily visually recognize an affected site obtained from the R, G, and B pixels and a pixel value for forming an image in which the operator may easily visually recognize the fluorescent thread 32 obtained from the NB pixel may be obtained by imaging once.

Then, an image processing unit 53 performs demosaic processing by using the pixel values of the R, G, and B pixels, thereby generating an RGB demosaic image in which the affected site is easily visually recognized, and also generates an NB interpolated image in which the fluorescent thread 32 is easily visually recognized by performing interpolation processing of interpolating the pixel value of NB to have the same resolution as that of the RGB demosaic image. Thereafter, the image processing unit 53 performs synthesis processing of synthesizing the RGB demosaic image and the NB interpolated image to generate a synthetic image as illustrated in FIG. 12, and outputs the same to an image output unit 54.

3. Other Configuration Example of Fluorescent Thread

In each of the embodiments described above, the fluorescent thread 32 is described as a material that uniformly shines in the same color in any part of an entire thread.

Figure 13:
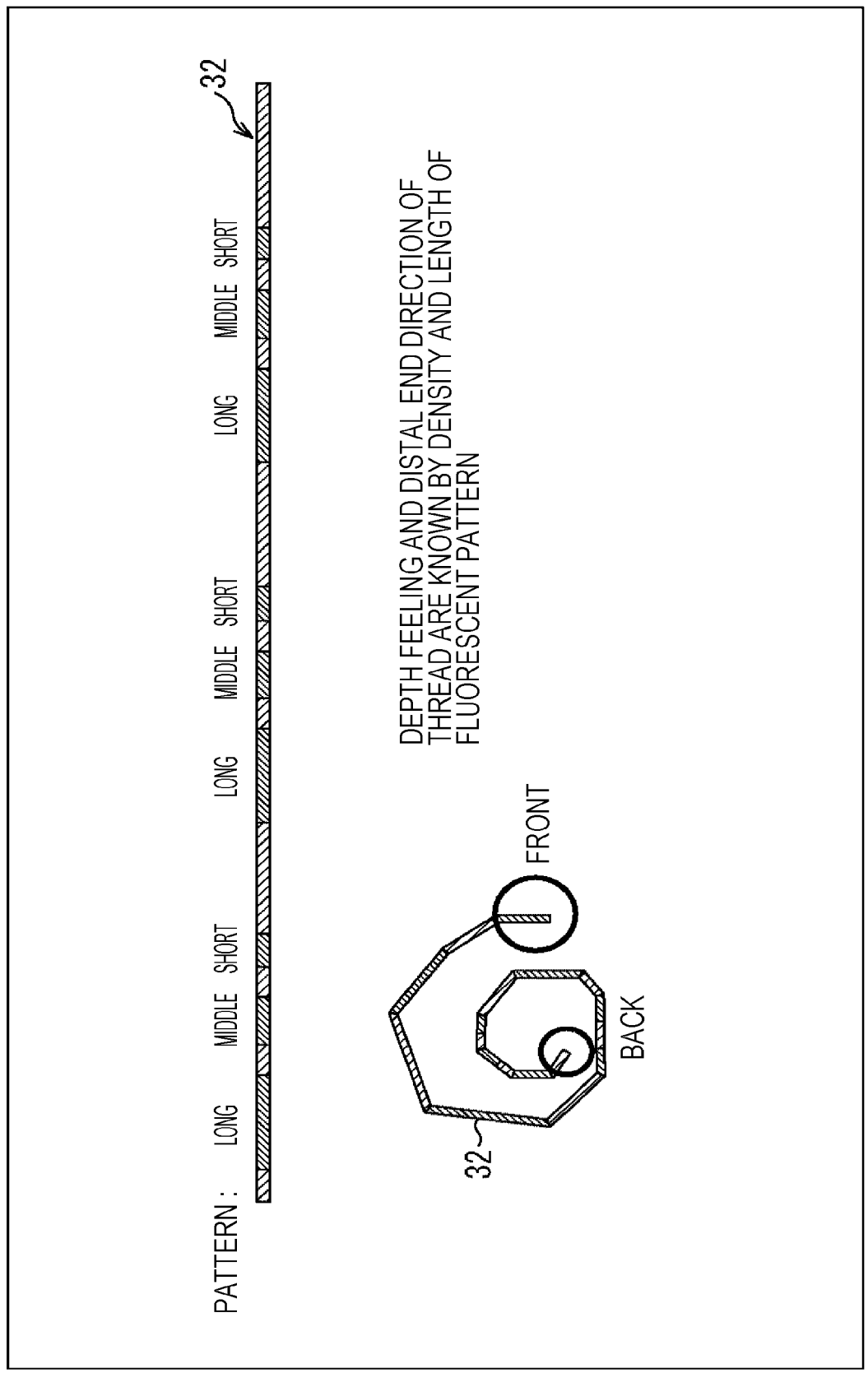
FIG. 13 is a view illustrating another configuration example of a fluorescent thread.

However, the fluorescent thread 32 may be configured to fluoresce in a repetitive pattern not present in a living body, for example, as illustrated in FIG. 13. The fluorescent thread 32 illustrated in FIG. 13 has a pattern in which a combination pattern of long, medium, short of a second fluorescent color different from a first fluorescent color is repeated at a predetermined interval between the first fluorescent color. Herein, long, medium, and short indicate difference in length in which the second fluorescent color continues in a longitudinal direction of the fluorescent thread 32.

In this manner, by configuring the fluorescent thread 32 to shine in the repetitive pattern not present in the living body, the operator may easily grasp depth feeling of the affected site and a distal end direction of the thread displayed as an image on the basis of density or a length of fluorescent patterns.

Figure 14:
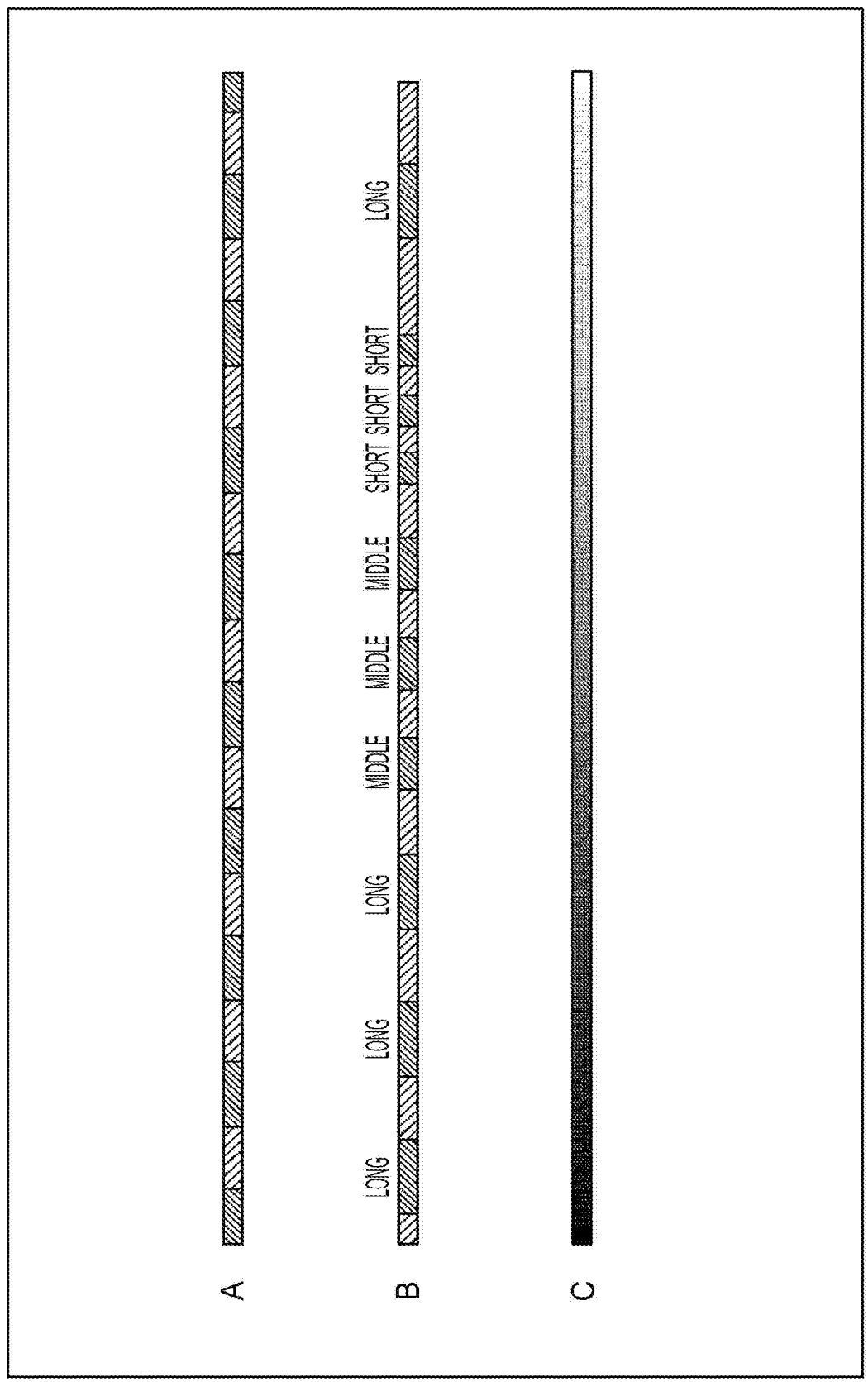
FIG. 14 is a view illustrating another configuration example of the fluorescent thread.

FIG. 14 illustrates another example of the repetitive pattern not present in the living body of the fluorescent thread 32.

A of FIG. 14 illustrates an example of the repetitive pattern having a configuration in which the first fluorescent color and the second fluorescent color of the same length are alternately arranged.

B of FIG. 14 illustrates a pattern in which three patterns of a first pattern of long, long, long, a second pattern of medium, medium, medium, and a third pattern of short, short, short in the second fluorescent color are repeated in turn among the first fluorescent color.

Meanwhile, A of FIG. 14 and B of FIG. 14 are merely examples of the repetitive patterns not present in the living body, and the number, the length, the type and the like of the repetitive pattern are not limited to those in this example. The repetitive pattern not present in the living body may be a pattern in which patterns in a plurality of fluorescent colors are arranged according to a predetermined rule.

C of FIG. 14 illustrates an example of the fluorescent thread 32 in which the fluorescent colors are not clearly distinguished but gradationally change. In C of FIG. 14, the colors may gradationally change along the entire length of the fluorescent thread 32, or the gradation in C of FIG. 14 may be repeated a plurality of times in the entire fluorescent thread 32. Such a pattern of the fluorescent thread 32 is also included in the repetitive pattern not present in the living body.

4. Variation of Synthesis Unit

Figure 15:
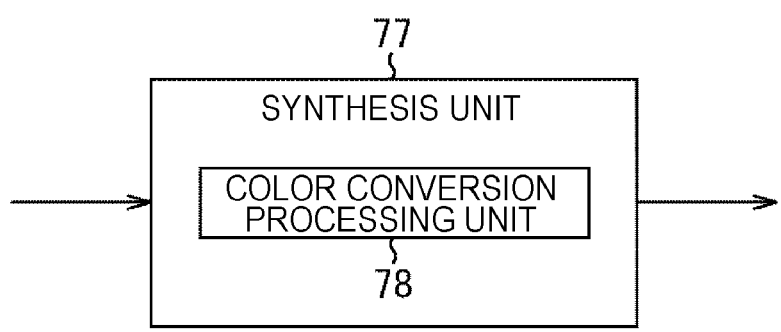
FIG. 15 is a block diagram illustrating a variation of a synthesis unit of an image processing unit.

FIG. 15 illustrates a variation of a synthesis unit 77 of an image processing unit 53.

The synthesis unit 77 is provided with a color conversion processing unit 78.

The color conversion processing unit 78 performs signal processing of converting a color of a fluorescent thread 32 in a synthetic image obtained by synthesizing a normal light image and a special light image so as to have a complementary color relationship with respect to a background color. In an operative site image, since the background of the fluorescent thread 32 is usually a patient's organ (living body) in a color of orange colors and red colors, the color conversion processing unit 78 converts the color of the fluorescent thread 32 to a color of blue colors and green colors which becomes a supplement to the color of the organ, for example.

Figure 16:
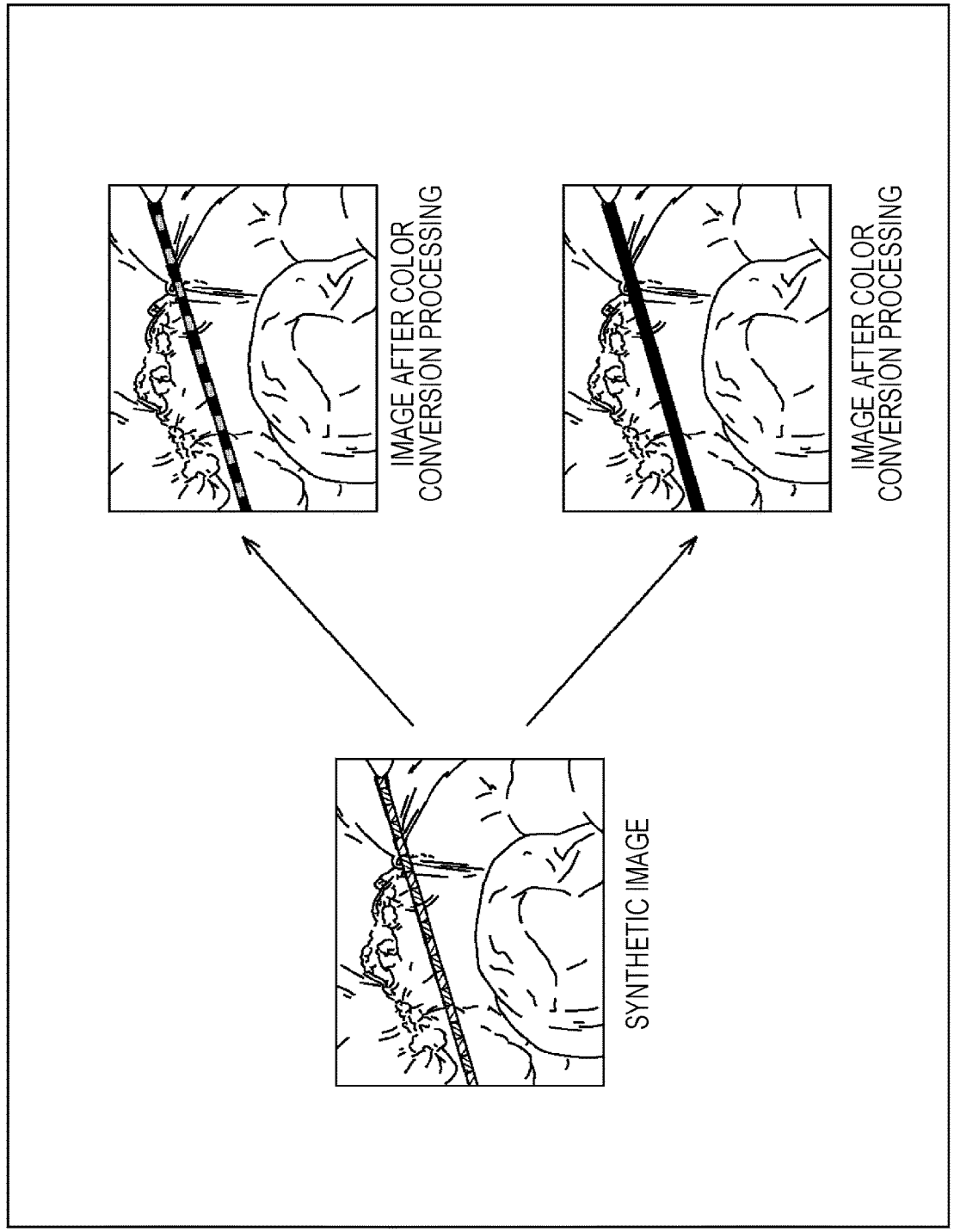
FIG. 16 is a view illustrating an example of an image after a color conversion processing.

FIG. 16 illustrates an example of the synthetic image intraoperatively generated in an operation using a thread having a repetitive pattern illustrated in A of FIG. 14 as the fluorescent thread 32, and an image after color conversion processing in which the color conversion processing unit 78 of the synthesis unit 77 performs the color conversion.

The image in an upper right part of FIG. 16 illustrates the image after color conversion processing in which a first fluorescent color (for example, yellow) and a second fluorescent color (for example, green) of the fluorescent thread 32 in the synthetic image are converted to a color equivalent to a first complementary color (for example, yellow green) and a color equivalent to a second complementary color (for example, blue), respectively.

The image in a lower right part of FIG. 16 illustrates the image after color conversion processing in which the first fluorescent color (for example, yellow) and the second fluorescent color (for example, green) of the fluorescent thread 32 in the synthetic image are converted to one color equivalent to the complementary color (for example, blue).

By replacing the fluorescent thread 32 in the synthetic image with the color taking the background color into consideration in this manner, the visibility of the fluorescent thread 32 may be further improved.

Also, the color conversion processing unit 78 may detect a position in a depth direction and a distal end of the fluorescent thread 32 by detecting density or a length of the repetitive pattern not present in a living body described with reference to FIGS. 13 and 14, thereby converting into different colors on a front side and a back side of the fluorescent thread 32 and converting into a different color on the distal end of the fluorescent thread 32 to display. This makes it easier for the operator to grasp the depth and the distal end of the fluorescent thread 32.

Meanwhile, although the color conversion processing unit 78 is a part of the synthesis unit 77 in FIG. 15, the color conversion processing unit 78 may also be provided on a subsequent stage of the synthesis unit 77.

5. Another Application Example of Color Conversion Processing

Another application example of the color conversion processing by the color conversion processing unit 78 is described.

At the time of suturing, it is important to determine antero-posterior positions of a needle tip and the thread (which is on a front side and which is on a back side), but grasping an antero-posterior relationship of the needle tip and the thread only by parallax during a long-time operation might cause fatigue of the operator.

Therefore, in a case where the thread is the fluorescent thread 32, since the fluorescent thread 32 emits light, it is possible to determine the antero-posterior relationship between the needle tip and the thread by determining whether reflection of the light from the fluorescent thread 32 is on the needle.

Figure 17:
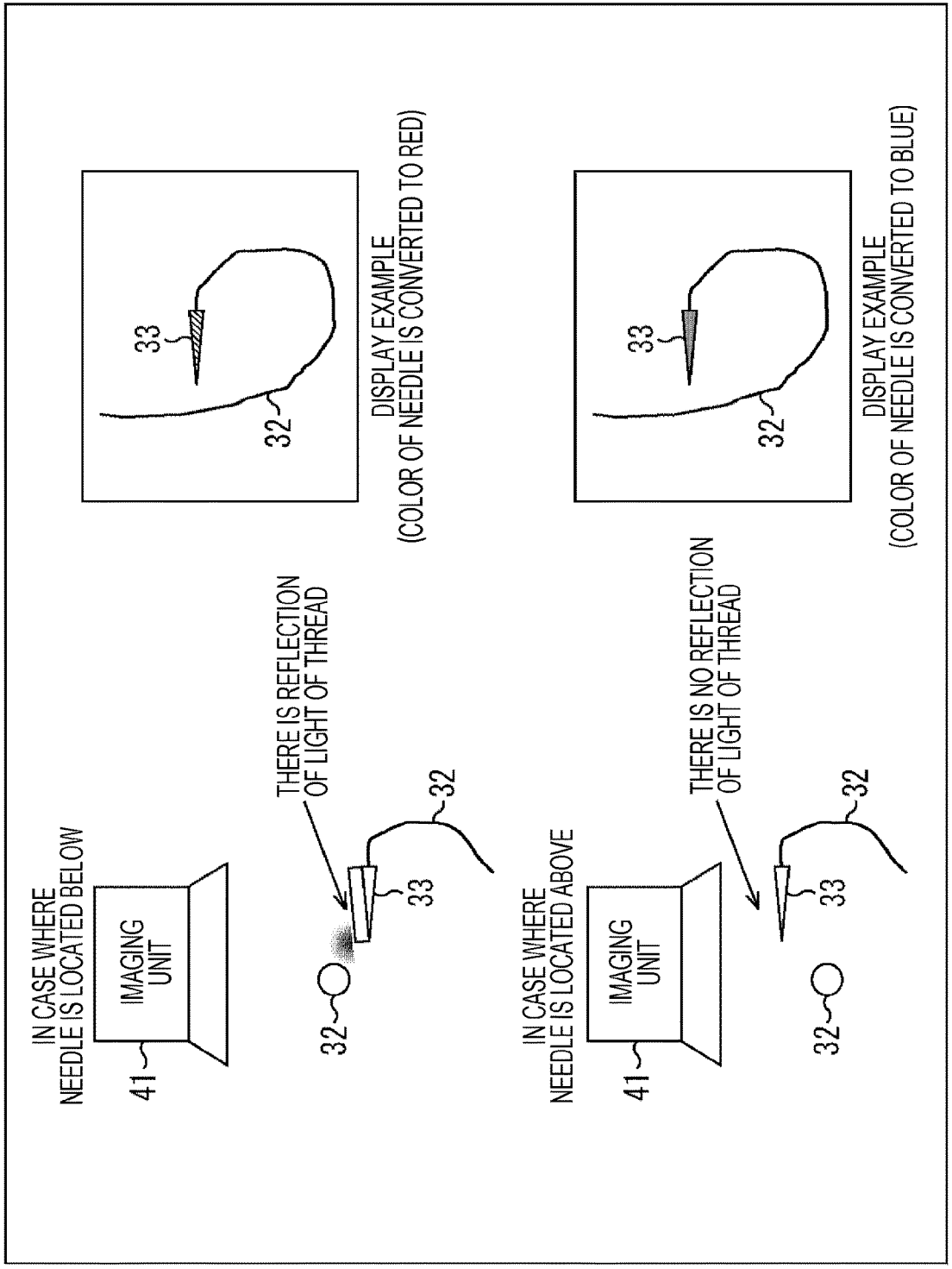
FIG. 17 is a view explaining another application example of the color conversion process.

Specifically, as illustrated in FIG. 17, in a case where a needle 33 is located below the fluorescent thread 32, in other words, in a case where the needle 33 is located at the back of the fluorescent thread 32 as seen from an imaging unit 41, there is the reflection of the light from the fluorescent thread 32 on the needle 33. On the other hand, in a case where the needle 33 is located above the fluorescent thread 32, in other words, in a case where the needle 33 is located in front of the fluorescent thread 32 as seen from the imaging unit 41, there is no reflection of the light from the fluorescent thread 32 on the needle 33.

In a case where it is determined that there is the reflection of the light from the fluorescent thread 32 on the needle 33, the color conversion processing unit 78 performs the color conversion such that the color of the needle 33 in the synthetic image is in a first color (for example, red), and in a case where it is determined that there is no reflection of the light from the fluorescent thread 32 on the needle 33, this performs the color conversion such that the color of the needle 33 in the synthetic image is in a second color (for example, blue).

Figure 18:
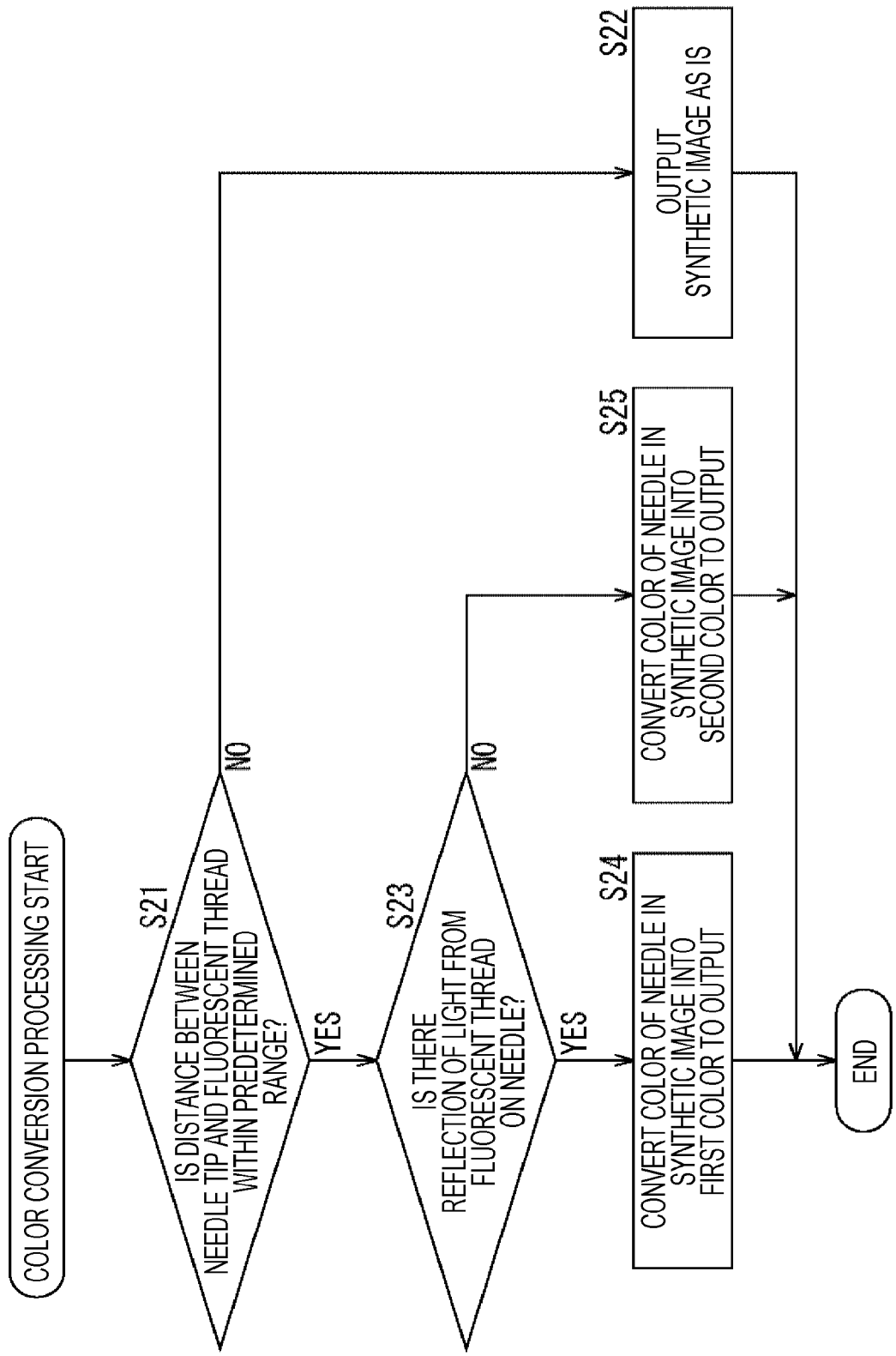
FIG. 18 is a flowchart explaining the color conversion processing.

FIG. 18 is a flowchart of the color conversion processing of converting the color of the needle in the synthetic image according to the antero-posterior relationship between the needle tip and the thread.

First, at step S21, the color conversion processing unit 78 detects the needle 33 and the fluorescent thread 32 in the synthetic image and determines whether a distance between a distal end of the needle 33 (needle tip) and the fluorescent thread 32 is within a predetermined range (distance).

Meanwhile, although a method of detecting the needle 33 in the synthetic image is not especially limited, it is assumed that the needle 33 in the synthetic image may be detected by some methods.

In a case where it is determined at step S21 that the distance between the distal end of the needle 33 and the fluorescent thread 32 is not within the predetermined range, the procedure shifts to step S22, and the color conversion processing unit 78 outputs the synthetic image as is to the image output unit 54 without performing the color conversion of the needle 33 in the synthetic image.

On the other hand, in a case where it is determined at step S21 that the distance between the distal end of the needle 33 and the fluorescent thread 32 is within the predetermined range, the procedure shifts to step S23, and the color conversion processing unit 78 determines whether there is the reflection of the light from the fluorescent thread 32 on the needle 33 in the synthetic image.

In a case where it is determined at step S23 that there is the reflection of the light from the fluorescent thread 32 on the needle 33, the procedure shifts to step S24, and the color conversion processing unit 78 converts the color of the needle 33 in the synthetic image to the first color (for example, red) and outputs the same.

On the other hand, in a case where it is determined at step S23 that there is no reflection of the light from the fluorescent thread 32 on the needle 33, the procedure shifts to step S25, and the color conversion processing unit 78 converts the color of the needle 33 in the synthetic image to the second color (for example, blue) and outputs the same.

By performing the above-described color conversion processing, the operator may easily grasp the antero-posterior relationship between the needle tip and the thread simply by discriminating the color of the needle 33 in the synthetic image displayed on a display device 11.

6. Fluorescent Thread Area Pixel Addition Processing

Generally, spontaneous light emitting materials are weak in light emission intensity, and there is a fear that images with a poor SN ratio may result due to an effect of sensor noise and the like. Therefore, in a case where there is little change in motion in an area of the fluorescent thread 32, the synthesis unit 77 may add pixel values of a plurality of consecutive images, thereby generating the synthetic image in which the SN ratio is increased and the visibility is improved.

Figure 19:
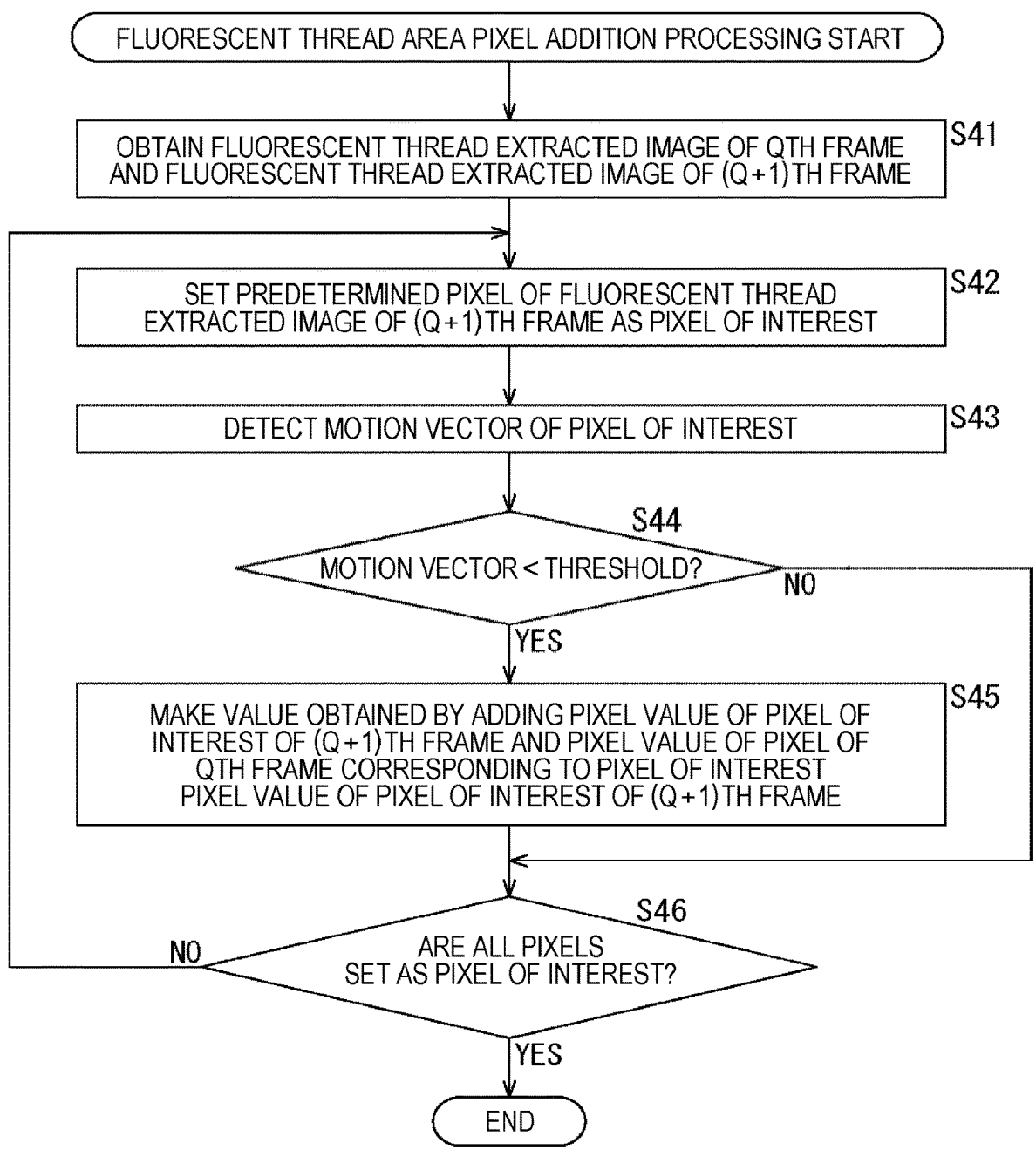
FIG. 19 is a flowchart explaining fluorescent thread area pixel addition processing.

FIG. 19 illustrates a flowchart of the fluorescent thread area pixel addition processing of adding the pixel value of the area of the fluorescent thread 32 in a case where there is little change in motion. This processing starts, for example, when the normal light image and a motion-corrected fluorescent thread extracted image are input to the synthesis unit 77.

First, at step S41, the synthesis unit 77 obtains the fluorescent thread extracted image of a Qth frame and the fluorescent thread extracted image of a (Q+1)th frame. Herein, the Qth and the (Q+1)th frames indicate the order in which only the fluorescent thread extracted images created from the special light images imaged at an interval of a plurality of images are counted, as illustrated in FIG. 4 and FIG. 10. Therefore, the synthesis unit 77 is required to hold the fluorescent thread extracted image of the immediately preceding Qth frame in an internal memory and the like until the fluorescent thread extracted image of the (Q+1)th frame is input from a motion correction unit 76.

At step S42, the synthesis unit 77 sets a predetermined pixel of the fluorescent thread extracted image of the (Q+1)th frame as a pixel of interest.

At step S43, the synthesis unit 77 detects a motion vector of the pixel of interest using the fluorescence thread extracted image of the Qth frame and the fluorescence thread extracted image of the (Q+1)th frame.

At step S44, the synthesis unit 77 determines whether the detected motion vector of the pixel of interest is smaller than a predetermined threshold set in advance.

In a case where it is determined at step S44 that the detected motion vector of the pixel of interest is smaller than the predetermined threshold, the procedure shifts to step S45, and the synthesis unit 77 makes a value obtained by adding the pixel value of the pixel of interest of the (Q+1)th frame to the pixel value of the pixel of the Qth frame corresponding to the pixel of interest the pixel value of the pixel of interest of the (Q+1)th frame.

On the other hand, in a case where it is determined at step S44 that the detected motion vector of the pixel of interest is equal to or larger than the predetermined threshold, the process at step S45 is skipped. In this case, the pixel value of the pixel of interest of the (Q+1)th frame is not changed (not added).

At step S46, the synthesis unit 77 determines whether all the pixels of the fluorescent thread extracted image of the (Q+1)th frame are set as the pixel of interest.

In a case where it is determined at step S46 that not all the pixels of the fluorescent thread extracted image of the (Q+1)th frame are set as the pixel of interest, the procedure returns to step S42, and steps S42 to 46 described above are repeated. That is, in the fluorescent thread extracted image of the (Q+1)th frame, a pixel which is not yet set as the pixel of interest is set as a next pixel of interest, the motion vector is detected, and the pixel value is added on the basis of a detection result.

Then, in a case where it is determined at step S46 that all the pixels of the fluorescent thread extracted image of the (Q+1)th frame are set as the pixel of interest, the fluorescent thread area pixel addition processing ends.

Figure 7:
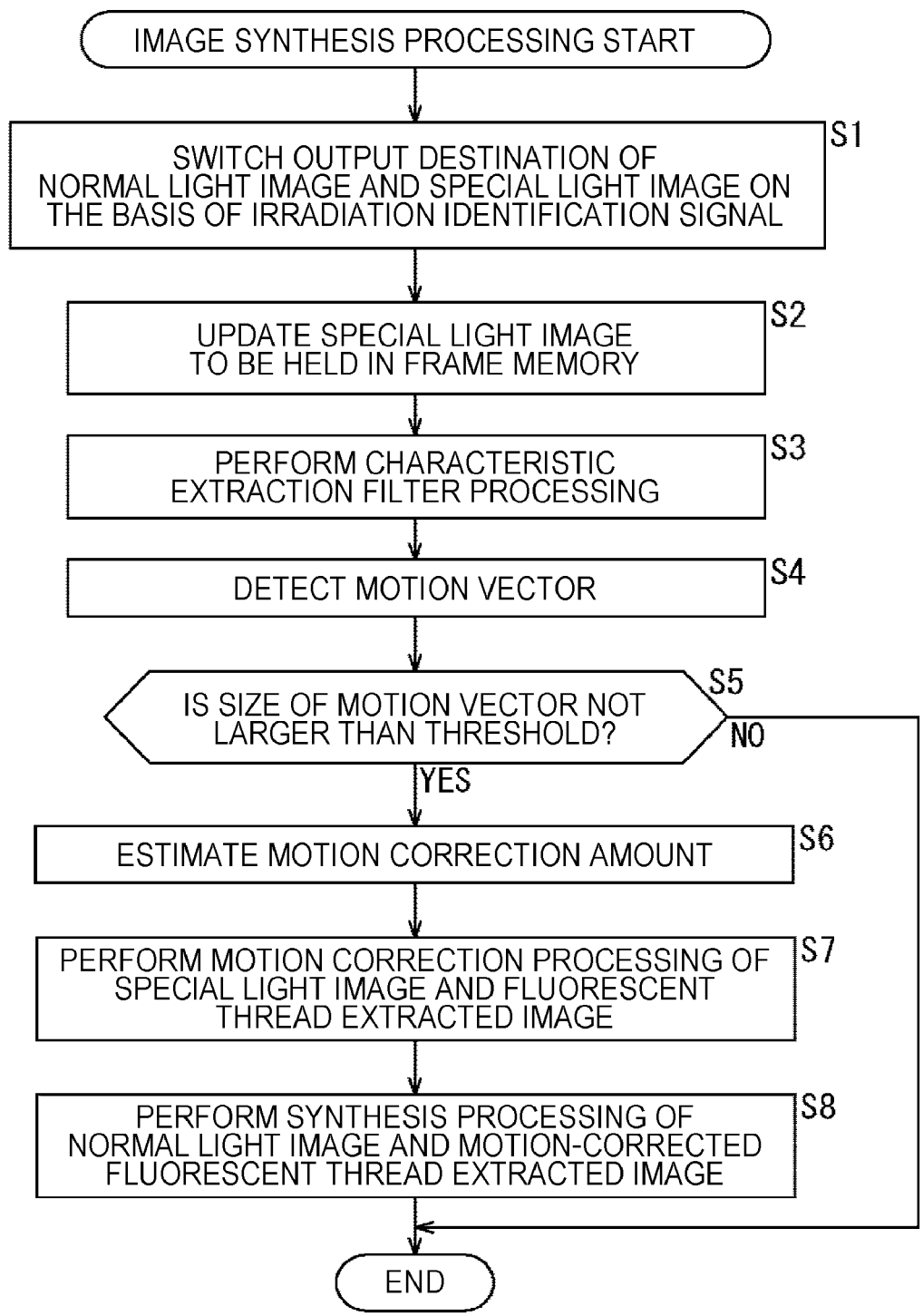
FIG. 7 is a flowchart explaining the image synthesis processing by the image processing unit.

This fluorescent thread area pixel addition processing may be executed, for example, between the process at step S7 and the process at step S8 of the image synthesis processing in FIG. 7. Furthermore, in the process at step S8 of the image synthesis processing in this case, the synthesis processing is performed to synthesize the fluorescent thread extracted image to which the pixel value is added and the normal light image for the area of the fluorescent thread 32 with little motion, and the synthetic image is generated.

Figure 20:
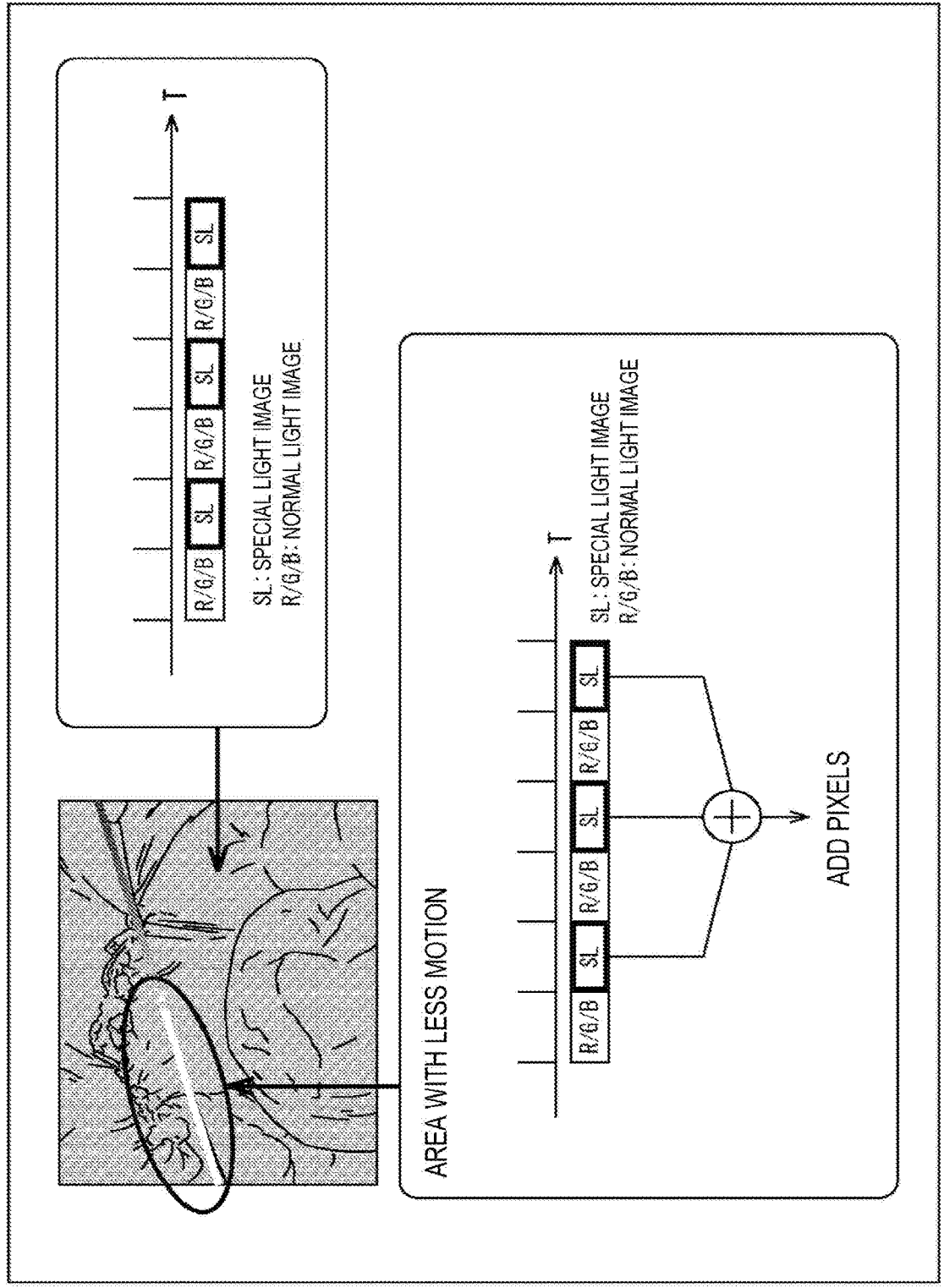
FIG. 20 is a view illustrating an example of the fluorescent thread area pixel addition processing.

FIG. 20 illustrates an example of the fluorescent thread extracted image after the fluorescent thread area pixel addition processing is executed.

In the fluorescent thread extracted image of FIG. 20, the luminance of an area with less motion out of the area of the fluorescent thread 32 is high. According to the fluorescent thread area pixel addition processing, it is possible to generate the synthetic image in which the SN ratio of the area of the fluorescent thread 32 with less motion is increased and the visibility is improved.

Meanwhile, the explanation of the fluorescent thread area pixel addition processing described above may be applied not only to the image synthesis processing of generating the normal light image and the special light image using an image sensor having a general Bayer array to create the synthetic image, but also to a case where an image sensor having pixels sensitive to light of a narrow band wavelength illustrated in FIG. 11.

The above-described series of processes may be executed by hardware or may be executed by software. In a case where a series of processes is executed by the software, a program which forms the software is installed on a computer. Herein, the computer includes a computer built in dedicated hardware, a general-purpose personal computer, for example, capable of executing various functions by various programs installed and the like.

FIG. 21 is a block diagram illustrating a configuration example of the hardware of the computer which executes the above-described series of processes by the program.

In a computer 100, a central processing unit (CPU) 101, a read only memory (ROM) 102, and a random-access memory (RAM) 103 are connected to one another through a bus 104.

An input/output interface 105 is further connected to the bus 104. An input unit 106, an output unit 107, a storage unit 108, a communication unit 109, and a drive 110 are connected to the input/output interface 105.

The input unit 106 includes a keyboard, a mouse, a microphone and the like. The output unit 107 includes a display, a speaker and the like. The storage unit 108 includes a hard disk, a non-volatile memory and the like. The communication unit 109 includes a network interface and the like. The drive 110 drives a removable medium 111 such as a magnetic disk, an optical disk, a magnetooptical disk, or a semiconductor memory.

In the computer 100 configured in the above-described manner, the CPU 101 loads the program stored in the storage unit 108, for example, on the RAM 103 through the input/output interface 105 and the bus 104 to execute, and thus, the above-described series of processes is performed.

The computer 100 may be a so-called cloud computer, for example, connected via the Internet.

Meanwhile, the program executed by the computer 100 may be the program of which processes are performed in chronological order in the order described in this specification or may be the program of which processes are performed in parallel or at necessary timing such as when a call is issued.

The embodiments of the present technology are not limited to the above-described embodiments and various modifications may be made without departing from the scope of the present technology.

The image synthesis processing to which the present technology is applied is similarly applicable to a surgery system using a video microscope in addition to the above-described endoscopic surgery system. In this case, a synthetic image may be generated using the special light image and the normal light image imaged by an imaging unit 41 of the video microscope.

In the above-described embodiments, the term of "frame period" is used as the imaging interval of the imaging by the imaging unit 41; however, the interval at which the imaging unit 41 generates the imaged image (the number of images generated per second) may be appropriately set.

All or a part of a plurality of embodiments and their variations described above may be combined as necessary.

The present technology may be configured as cloud computing in which one function is shared by a plurality of devices through the network to process together.

Also, each step described in the above-described flowchart may be executed by one device or executed by a plurality of devices in a shared manner.

Furthermore, in a case where a plurality of processes is included in one step, a plurality of processes included in one step may be executed by one device or by a plurality of devices in a shared manner.

Meanwhile, the effects described in this specification are illustrative only and are not limited; the effects other than those described in this specification may also be included.

In this specification, a system is intended to mean assembly of a plurality of components (devices, modules (parts) and the like) and it does not matter whether all the components are in the same casing. Therefore, a plurality of devices stored in different casings connected through the network and one device obtained by storing a plurality of modules in one casing are the systems.

Meanwhile, the present technology may also have following configurations.

(1)

An image processing device provided with:

an image obtaining unit which obtains a first image imaged under an illumination condition in which a surgical thread fluoresces and a second image imaged under an illumination condition including at least visible light as images of an operative site using the surgical thread which fluoresces; and a synthesis unit which generates a synthetic image obtained by synthesizing an area of the surgical thread of the first image and the second image.

(2)

The image processing device according to (1) described above, in which the first image is an image imaged under an illumination condition irradiated with light of a narrow band wavelength other than the visible light.

(3)

The image processing device according to (1) described above, in which the first image is an image generated by using a pixel signal of a narrow band pixel out of signals imaged by an image sensor including an RGB pixel which receives light of a wavelength of R, G, or B and the narrow band pixel which receives light of a narrow band wavelength other than the visible light, and the second image is an image generated using a pixel signal of the RGB pixel.

(4)

The image processing device according to any one of (1) to (3) described above, in which the surgical thread fluoresces in a pattern not present in a living body.

(5)

The image processing device according to (4) described above, in which the pattern is a pattern in which a second fluorescent color different from a first fluorescent color is repeated between the first fluorescent color.

(6)

The image processing device according to (4) described above, in which the pattern is a gradation pattern of fluorescent colors.

(7)

The image processing device according to any one of (1) to (6) described above, further provided with:

a color conversion processing unit which converts a color of the surgical thread in the synthetic image into a predetermined color.

(8)

The image processing device according to (7) described above, in which the color conversion processing unit performs color conversion such that a complementary color relationship with a background color is realized.

(9)

The image processing device according to (7) described above, in which the surgical thread fluoresces in a pattern not present in a living body, and the color conversion processing unit converts respective colors of the pattern into different colors.

(10)

The image processing device according to any one of (1) to (9) described above, further provided with:

a color conversion processing unit which converts a color of a needle of the synthetic image according to an anteroposterior relationship between the surgical thread and the needle.

(11)

The image processing device according to any one of (1) to (10) described above, in which the synthesis unit generates the first image in which pixel values of a plurality of first images are added for an area of the surgical thread with less motion, and generates the synthetic image obtained by synthesizing the first image to which the pixel values are added and the second image.

(12)

An image processing method provided with steps of:

obtaining a first image imaged under an illumination condition in which a surgical thread fluoresces and a second image imaged under an illumination condition including at least visible light as images of an operative site using the surgical thread which fluoresces; and generating a synthetic image obtained by synthesizing an area of the surgical thread of the first image and the second image.

(13)

A surgery system provided with:

an imaging unit which images a first image imaged under an illumination condition in which a surgical thread fluoresces and a second image imaged under an illumination condition including at least visible light as images of an operative site using the surgical thread which fluoresces; and a synthesis unit which generates a synthetic image obtained by synthesizing an area of the surgical thread of the first image and the second image.

(14)

The surgery system according to (13) described above, further provided with:

a light source device which emits light of a narrow band wavelength other than the visible light in a case where the first image is imaged and emits light at least including the visible light in a case where the second image is imaged.

(15)

The surgery system according to (13) described above, in which the imaging unit includes an image sensor including an RGB pixel which receives light of a wavelength or R, G, or B and a narrow band pixel which receives light of a narrow band wavelength other than the visible light.

(16)

A surgical thread which fluoresces in a pattern not present in a living body.

(17)

The surgical thread according to (16) described above, in which the pattern is a pattern in which a second fluorescent color different from a first fluorescent color is repeated between the first fluorescent color.

(18)

The surgical thread according to (16) described above, in which the pattern is a gradation pattern of fluorescent colors.

REFERENCE SIGNS LIST

10 Endoscopic surgery system
11 Display device
13 Light source device
19 Endoscope
32 Fluorescent thread
33 Needle
41 Imaging unit
51 Control unit
52 Image obtaining unit
53 Image processing unit
54 Image output unit
72 Motion vector detection unit
75 Characteristic extraction filter processing unit
77 Synthesis unit
78 Color conversion processing unit
100 Computer
101 CPU
102 ROM
103 RAM
106 Input unit
107 Output unit
108 Storage unit
109 Communication unit
110 Drive

The invention claimed is:

1. An image processing device comprising:
processing circuitry configured to
obtain, as images of an operative site in which a surgical thread which fluoresces is used, a first image imaged under a first illumination condition in which the surgical thread fluoresces and a second image imaged under a second illumination condition in which at least visible light is used to illuminate the operative site;
generate a synthetic image obtained by synthesizing the second image and an area of the surgical thread of the first image; and
convert, in the synthetic image, a color of the surgical thread into a predetermined color, wherein
the surgical thread fluoresces in a pattern not present in a living body, and
the processing circuitry is configured to convert respective colors of the pattern into different colors.

2. The image processing device according to claim 1, wherein, under the first illumination condition, the operative site is irradiated with light other than the visible light.

3. The image processing device according to claim 1, wherein the processing circuitry is configured to perform color conversion such that a complementary color relationship with a background color is realized.

4. The image processing device according to claim 1, further comprising
an imaging sensor which images the first image and the second.

5. The image processing device according to claim 1, further comprising:
a light source device which emits light to illuminate the operative site.

6. An image processing device comprising:
processing circuitry configured to obtain, as images of an operative site in which a surgical thread which fluoresces is used, a first image imaged under a first illumination condition in which the surgical thread fluoresces and a second image imaged under a second illumination condition in which at least visible light is used to illuminate the operative site;
generate a synthetic image obtained by synthesizing the second image and an area of the surgical thread of the first image; and
convert a color of a needle of the synthetic image according to an antero-posterior relationship between the surgical thread and the needle.

7. A surgical thread which fluoresces in a pattern not present in a living body, wherein the pattern is either:
a pattern in which a region of a second fluorescent color is repeated between regions of a first fluorescent color, the first fluorescent color being different from the second fluorescent color, or
a gradation pattern of fluorescent colors.

* * * * *